(12) United States Patent
Chen et al.

(10) Patent No.: US 7,125,885 B2
(45) Date of Patent: *Oct. 24, 2006

(54) FUSED HETEROCYCLIC COMPOUNDS

(75) Inventors: Xiaoqi Chen, San Mateo, CA (US); Pingchen Fan, Fremont, CA (US); Juan Jaen, Burlingame, CA (US); Leping Li, Burlingame, CA (US); Mike Lizarzaburu, San Bruno, CA (US); Jeffrey Thomas Mihalic, San Francisco, CA (US); Stephen Joseph Shuttleworth, Foster City, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/928,029

(22) Filed: Aug. 26, 2004

(65) Prior Publication Data

US 2005/0148617 A1   Jul. 7, 2005

Related U.S. Application Data

(63) Continuation of application No. 10/289,933, filed on Nov. 6, 2002, now Pat. No. 6,809,104, which is a continuation-in-part of application No. 10/138,279, filed on May 3, 2002, now Pat. No. 6,858,619.

(51) Int. Cl.
  *C07D 471/04* (2006.01)
  *A61K 31/437* (2006.01)
(52) U.S. Cl. .......................... 514/285; 546/70
(58) Field of Classification Search ............... 546/70; 514/285
See application file for complete search history.

(56) References Cited

U.S. PATENT DOCUMENTS

| | | | |
|---|---|---|---|
| 4,115,538 A | 9/1978 | Satoh et al. | |
| 5,049,655 A | 9/1991 | Vaughan et al. | |
| 5,272,146 A | 12/1993 | Haugwitz et al. | |
| 5,436,128 A | 7/1995 | Harpold et al. | |
| 5,441,956 A | 8/1995 | Vecchietti et al. | |
| 5,449,766 A | 9/1995 | Vaughan et al. | |
| 5,457,208 A | 10/1995 | Portoghese et al. | |
| 5,530,095 A | 6/1996 | Vaughn et al. | |
| 5,849,708 A | 12/1998 | Maratos-Flier | |
| 6,033,872 A | 3/2000 | Bergsma et al. | |
| 6,809,104 B1 * | 10/2004 | Chen et al. ............. | 514/285 |
| 2003/0023085 A1 | 1/2003 | Chen et al. | |
| 2003/0176694 A1 | 9/2003 | Chen et al. | |
| 2003/0199549 A1 | 10/2003 | Burnett et al. | |
| 2004/0147538 A1 | 7/2004 | Chen et al. | |

FOREIGN PATENT DOCUMENTS

| EP | 0 257 701 | 8/1987 |
|---|---|---|
| EP | 02 73 4135 | 4/2005 |
| EP | 02 734 1353 | 12/2005 |
| JP | 4-368384 | 12/1992 |
| JP | 2001226269 | 8/2001 |
| WO | WO91/07966 | 6/1991 |
| WO | WO94/07896 | 4/1994 |
| WO | WO95/13071 | 5/1995 |
| WO | WO96/23793 | 8/1996 |
| WO | WO98/31684 | 7/1998 |
| WO | WO99/28492 | 12/1998 |
| WO | WO99/64002 | 6/1999 |
| WO | WO00/15793 | 9/1999 |
| WO | WO00/22129 | 10/1999 |
| WO | WO00/39279 | 12/1999 |
| WO | WO00/40725 | 12/1999 |
| WO | WO00/49170 | 1/2000 |
| WO | WO00/21577 | 4/2000 |
| WO | WO00/75166 | 6/2000 |
| WO | WO01/05947 | 7/2000 |
| WO | WO01/07606 | 7/2000 |
| WO | WO01/07611 | 7/2000 |
| WO | WO00/49046 | 8/2000 |
| WO | WO01/21577 | 9/2000 |
| WO | WO00/70347 | 11/2000 |
| WO | WO01/36479 | 11/2000 |
| WO | WO01/21169 | 3/2001 |
| WO | WO01/68706 | 3/2001 |
| WO | WO01/70975 | 3/2001 |
| WO | WO01/87834 | 11/2001 |

(Continued)

OTHER PUBLICATIONS

Yuguang Shi {Peptides 25 (2004) 1605-1611}.*

(Continued)

*Primary Examiner*—Kahsay Habte
(74) *Attorney, Agent, or Firm*—Jones Day

(57) ABSTRACT

The present invention provides compounds having the formula:

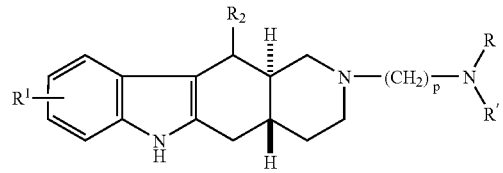

wherein $R^1$, $R^2$, R, R' and the subscript p are described herein. The compounds are useful in the treatment and/or prevention of a condition or disorder mediated by a G-protein coupled receptor. Pharmaceutical compositions and methods of using these compounds for the treatment and/or prevention of a condition or disorder mediated by a G-protein coupled receptor, such as eating disorder, obesity, anxiety disorders and mood disorders are also provided.

2 Claims, 2 Drawing Sheets

FOREIGN PATENT DOCUMENTS

| WO | WO02/002744 | 1/2002 |
|----|----|----|
| WO | WO02/03070 | 1/2002 |
| WO | WO02/04433 | 1/2002 |
| WO | WO02/06245 | 1/2002 |
| WO | WO02/032897 | 4/2002 |
| WO | WO02/051809 | 7/2002 |
| WO | WO02/057233 | 7/2002 |
| WO | WO02/076929 | 10/2002 |
| WO | WO02/076947 | 10/2002 |
| WO | WO02/083134 | 10/2002 |
| WO | WO02/094799 | 11/2002 |
| WO | WO02089729 | 11/2002 |
| WO | WO03/060475 | 7/2003 |
| WO | PCT/US03/35543 | 4/2004 |

OTHER PUBLICATIONS

Aceto, MD et al., "Dependence studies of new compounds in the Rhesus monkey, rat and mouse", (1997) Department of Pharmacology and Toxicology, Medical College of Virginia Commonwealth University, pp. 363-407.

Bergman et al., 1980 ACTA Chemica Scandinavica, Series B; Organic Chemistry and Biochemistry B34(10):763-66.

Berridge, et al. "Inositol Triphosphate, a Novel Second Messenger In Cellular Signal Transduction", Nature (1984) 312:315-321.

Blechert, S. et al., "Domino reactions—New concepts in the synthesis of indole alkaloids and other polycyclic indole derivatives", (1995) Insitut Für Organische Chemie, Sekr. C3, Technische Universität Berlin, Straβe des 17 Juni 135, D-10623 Berlin, Germany pp. 592-604.

Boutin et al., (2002) "Melanin-Concentrating Hormone and its Receptors: State of the Art," Can, J. of Physio. and Pharmacol. 80: 388-395.

Chambers, et al. "Melanin-concentrating hormone is the cognate ligand for the orphan G-protein-coupled receptor SLC-1", Nature (1999) 400: 261-265.

Chambers et al., "Melanin-concentrating hormone is the cognate ligand for the orphan G-protein-coupled receptor SLC-1" Nature, (1999) 400:261-65.

Felley-Bosco, et al. "Constitutive Expression of Inducible Nitric Oxide Synthase in Human Brochial Epithelial Cells Induces c-fos and Stimulates the cGMP Pathway", Am J. Respir Cell. Mol. Biol. (1994) 11: 159-164.

Fujii, H. et a., "A novel abnormal rearrangement in the fishcer indole synthesis", (1997) Heterocycles 45:2109-2112.

Gonzalez, et al. "alpha-Melanocyte-stimulating hormone (alpha-MSH) and melanin-concentrating hormone (MCH) modify monoaminergic levels in the preoptic area of the rat" Peptides (1997) 18:387-392.

Gonzalez, et al., "Behavioral Effects of α-MSH and MCH After Central Administration in the Female Rat" Peptides (1996) 17(1):171-177.

Gouyette, A. et al., "Synthesis, DNA intercalation and antitumor activity of 9-hdroxy-11-demethylellipticine and some derivatives. Comparison with the corresponding ellipticines", (1980) Euro. J. Med. Chem. 15:503-510.

Guillonneau, C. et al., "Synthesis of 9-O-substituted derivatives of 9-hydroxy-5,6-dimethyl-6H-pyrido[4,3-b]carbazole-l-carboxylic acid (2-(dimethylamino)ethyl)amide and their 10-and 11-methyl analogues with improved anititumor activity", (1990) J. Med. Chem. 42:2191-2203.

Ishikura et al., "A Novel Entry to Pyrido [4,3-b] Carbazole: An Efficient Synthesis of Ellipticine", Chemical Abstract, vol. 132, Abstract 237230, 2000.

Jones, RM et al., "5'-Guanidinonaltrindole, a highly selective and potent k-opioid receptor atagonist"(2000) Euro. J. Med. Chem. 396:49-52.

Langlois et al., (975) Tetrahedron Letters 11: 955-958.

Lipkowski, A W et al., "Benzomorphan alkaloids: natural peptidomimetics of opioid peptide pharmacophores", (1995) Letters in Peptide Science, 2:177-181.

Monzon, et al., "Response to Novelty After I.C.V. Injection of Melanin-Concentrating Hormone (MCH) in Rats" Physiol. Behav. (1999) 67(5):813-817.

Offerman, et al. "$G\alpha_{15}$ and $G\alpha_{16}$ Couple A Wide Variety of Receptors to Phospholipase C", The J. of Biological chemistry (1995), 270(25) pp. 15175-15180.

Olmsted, SL et al., "A remarkable change of opioid receptor selectivity on the attachment of a peptidomimetric κ address element to the δ antagonist, naltrindole: 5'-[($N^2$-alkylamidino)methyl]naltrindole derivatives as a novel class of κ opioid receptor antagonists" (1993) J. Med. Chem. 36:179-180.

Portoghese, PS et al., "Naltrindole 5'-isothiocyanate: a nonequilibrium, higly selective δ opioid receptor antagonist" (1990) J. Med. Chem. 33:1547-1548.

Portoghese, PS et al., "Design of peptidomimetic δ opioid receptor antagonists using the message-address concept" (1990) J. Med. Chem. 33:1714-1720.

Portoghese, PS et al., "Application of the message-address concept in the design of highly potent and selective non-peptide δ opioid receptor antagonists", (1988) J. Med. Chem. 31:281-282.

Portoghese, PS et al., "7'-substituted amino acid conjugates of naltrindole. Hydrophillic groups as determinants of selective antagonism of δ, opioid receptor-mediated antinociception in mice." (1995) J. Med. Chem. 38:402-407.

Rai, et al., "Synthesis, P {hysicochemical Properties, and Evaluation of N-Substituted-2-Alkyl-3-Hydroxy-4(1H)-Pyridones" J.. Med. Chem. (1998) 41:3347-3359.

Rastogi, et al. 1987 "Synthesis, Neuroleptic & Antiinflammatory Activites of 4a, 11a-cis-&trans-2-[γ-(p-Fluorobenzoyl)proppyl]-1,2,3,4,4a,5,11,11 a-octahydro-6H-pyriod[4,3-b]carbazoles & Related Derivatives," India Journal of Chemistry 26B: 335-340.

Saito, et al. "Molecular characterization of the melanin-concentrating-hormone receptor", Nature(1999) 400: 265-269.

Saito, et al., "Melanin-concentrating hormone receptor: an orphan receptor fits the key" Trends Endocrinol. Metab. (2000) 11(8): 299-303.

Série G "Chimie Organique.—Une nouvelle synthèse du système 6 H-pyrido-(4.3b) carbaxolique", (1972) C.R. Acad. Sc. Paris, t. 274:1948-1949.

Seyferth, et al., "Some Reactions of Dimethylphosphono-Substituted Diazoalkanes. $(MeO)_2P(O)CR$ Transfer to Olefins and 1,3-Dipolar Additions of $(MeO)_2P(O)C(N_2)R^{1}$", J. Org. Chem. (1971) 36(10): 1379-1386.

Shimada, et al., "Mice Lacking melanin-concentrating hormone are Hypophagic and Lean", Nature (1998) 396:670-674.

Stevens, WC et al., "Potent and selective indolopmorphinan antagonists of the kappa-opioid receptor", (2000) J. Med. Chem. 43: 2759-2769.

Wilkie, et al., "Characterization of G-Protein αSubunits in the $G_q$ Class: Expression in Murine Tissues and In Stromal and Hematopoietic Cell Lines", Proc. Natl. Acad. Sci. USA (1991) 88: pp. 10049-10053.

Sainsbury, Malcom, 1977 "The Synthesis of 6H-Pyrido[4,3-b]Carbazoles" Synthesis, 7: 437-448.

Rastogi et al., 1972 "A New Synthesis of 6H-Pyrido[4,3-b]Carbazoles," Indian Journal of Chemistry, 10:673-674.

Ishikura et al., 2000 "A Novel Entry to [4,3-b]Carbazoles: An Efficient Synthesis of Ellipticine" Tetrahedron, 56:193-207.

* cited by examiner

FUSED HETEROCYCLIC COMPOUNDS

CROSS-REFERENCE TO RELATED APPLICATIONS

This application is a continuation of, and claims the benefit under 35 U.S.C. § 120 of, U.S. application Ser. No. 10/289,933, filed Nov. 6, 2002 now U.S. Pat. No. 6,809,104, which is a continuation-in-part of U.S. patent application Ser. No. 10/138,279, filed May 3, 2002 now U.S. Pat. No. 6,858,619, and is related to International Application No. PCT/US02/13856, filed May 3, 2002, which claim the benefit of U.S. Application Ser. No. 60/288,665, filed May 4, 2001, the disclosures of which are incorporated herein by reference.

FIELD OF THE INVENTION

The present invention relates to compounds, compositions and methods useful in the treatment or prevention of conditions and disorders associated with eating behavior, energy homeostasis and anxiety.

BACKGROUND OF THE INVENTION

G-protein coupled receptors play important roles in diverse signaling processes, including those involved with sensory and hormonal signal transduction. Eating disorders, which represent a major health concern throughout the world, have been linked to GPCR regulation. On the one hand, disorders such as obesity, the excess deposition of fat in the subcutaneous tissues, manifest themselves by an increase in body weight. Individuals who are obese often have, or are susceptible to, medical abnormalities including respiratory difficulties, cardiovascular disease, diabetes and hypertension. On the other hand, disorders like cachexia, the general lack of nutrition and wasting associated with chronic disease and/or emotional disturbance, are associated with a decrease in body weight.

The neuropeptide melanin-concentrating hormone (MCH), a cyclic hypothalamic peptide involved in the regulation of several functions in the brain, has previously been found to be a major regulator of eating behavior and energy homeostasis. It has previously been determined that MCH is the natural ligand for the 353-amino acid orphan G-protein-coupled-receptor (GPCR) termed SLC-1 (also known as GPR24). Subsequent to this determination, SLC-1, which is sequentially homologous to the somatostatin receptors, is frequently referred to as melanin-concentrating hormone receptor (MCH receptor, MCHR or MCHR1) (see Chambers et al., Nature 400:261–65 (1999); Saito et al., Nature 400:265–69 (1999); and Saito et al., TEM 11(8): 299–303 (2000)).

Compelling evidence exists that MCH is involved in regulation of eating behavior. First, intracerebral administration of MCH in rats resulted in stimulation of feeding. Next, mRNA corresponding to the MCH precursor is up-regulated in the hypothalamus of genetically obese mice and of fasted animals. Finally, mice deficient in MCH are leaner and have a decreased food intake relative to normal mice. MCH is believed to exert its activity by binding to MCHR, resulting in the mobilization of intracellular calcium and a concomitant reduction in cAMP levels (see Chambers et al., Nature 400:261–65 (1999); Shimada et al. Nature 396: 670–74 (1998)). MCH also activates inwardly rectifying potassium channels, and MCHR has been found to interact with both Gαi protein and Gαq protein (Saito et al., TEM 11(8):299–303 (2000)). Moreover, analysis of the tissue localization of MCHR indicates that it is expressed in those regions of the brain involved in olfactory learning and reinforcement. The cumulative data suggest that modulators of MCHR should have an effect on neuronal regulation of food intake (see Saito et al., Nature 400:265–69 (1999)).

MCH has been shown to modulate behaviors other than feeding, such as anxiety (Gonzales et al. (1996) Peptides 17:171–177; Monzon et al. (1999) Physiol. Behav. 67:813–817).

The identification of MCHR modulators is useful for the study of physiological processes mediated by MCHR and the development of therapeutic agents for the treatment or prevention of conditions and disorders associated with weight regulation, learning, anxiety and other neuronal-related functions.

SUMMARY OF THE INVENTION

The present invention provides fused heterocyclic compounds and compositions, and methods of use thereof to treat or prevent conditions and disorders mediated by MCHR. In particular, the present invention provides compounds, compositions and methods for treating or preventing conditions and disorders associated with eating behavior, energy homeostasis and anxiety.

The compounds provided herein have the formula (I):

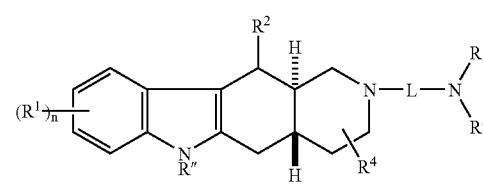

wherein

L is a bond or $(C_1-C_4)$alkylene;

R and R' are independently selected from the group consisting of hydrogen, $(C_1-C_8)$alkyl, $(C_2-C_8)$alkenyl, $(C_2-C_8)$alkynyl, $CO_2R^{13}$, $SO_2R^{13}$, $C(O)NR^{13}R^{14}$, $SO_2NR^{13}R^{14}$ and $(C_1-C_4)$alkylene-$CO_2R^{13}$;

optionally, R and R' may be combined to form a 3-, 4-, 5-, 6- or 7-membered ring containing the nitrogen atom and from 0 to 2 additional heteroatoms selected from the group consisting of N, O and S;

R" is hydrogen or $(C_1-C_8)$alkyl;

each $R^1$ is independently selected from the group consisting of halogen, $(C_1-C_8)$alkyl, $(C_2-C_8)$alkenyl, $(C_2-C_8)$alkynyl, fluoro$(C_1-C_4)$alkyl, $-OR^5$, $-SR^5$, fluoro$(C_1-C_4)$alkoxy, aryl, aryl$(C_1-C_4)$alkyl, $-NO_2$, $-NR^5R^6$, $-C(O)R^5$, $-CO_2R^5$, $-C(O)NR^5R^6$, $-N(R^6)C(O)R^5$, $-N(R^6)CO_2R^5$, $-N(^7)C(O)NR^5R^6$, $-S(O)_mNR^5R^6$, $-S(O)_mR^5$, $-CN$ and $-N(R^6)S(O)_mR^5$;

$R^2$ is selected from the group consisting of halogen, $(C_1-C_8)$alkyl, $(C_2-C_8)$alkenyl, $(C_2-C_8)$alkynyl, fluoro$(C_1-C_4)$alkyl, $-OR^8$, $-SR^8$, fluoro$(C_1-C_4)$alkoxy, aryl, aryl$(C_1-C_4)$alkyl, $-NO_2$, $-NR^8R^9$, $=O$, $-C(O)R^8$, $-CO_2R^8$, $-C(O)NR^8R^9$, $-N(R^9)C(O)R^8$, $-N(R^9)CO_2R^8$, $-N(R^{10})C(O)NR^8R^9$, $-S(O)_mNR^8R^9$, $-S(O)_mR^8$, $-CN$ and $-N(R^9)S(O)_mR^8$;

$R^4$ is selected from the group consisting of hydrogen $-OR^{11}$, $-C(O)R^{11}$, $-CO_2R^{11}$, $-C(O)NR^{11}R^{12}$, $-CN$, $(C_1-C_4)$alkyl and aryl;

$R^5$, $R^6$, $R^7$, $R^8$, $R^9$, $R^{10}$, $R^{11}$, $R^{12}$, $R^{13}$, $R^{14}$, $R^{16}$ and $R^{17}$ are independently selected from the group consisting of hydrogen, $(C_1-C_8)$alkyl, $(C_2-C_8)$alkenyl, $(C_2-C_8)$alkynyl, fluoro$(C_1-C_4)$alkyl, hetero$(C_1-C_4)$alkyl, aryl and aryl$(C_1-C_4)$alkyl;

optionally, when two R groups selected from the group consisting of $R^5$, $R^6$, $R^7$, $R^8$, $R^9$, $R^{10}$, $R^{11}$, $R^{12}$, $R^{13}$ and $R^{14}$ are attached to the same nitrogen atom, the R groups may be combined to form a 3-, 4-, 5-, 6- or 7-membered ring containing the nitrogen atom and from 0 to 2 additional heteroatoms selected from the group consisting of N, O and S;

the subscript m is 1 or 2; and the subscript n is 0, 1 or 2.

Also provided herein are compounds of formula (II):

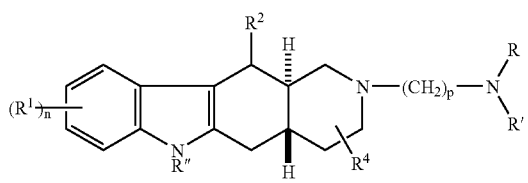

wherein

R and R' are independently selected from the group consisting of hydrogen, $(C_1-C_8)$alkyl, $(C_2-C_8)$alkenyl, $(C_2-C_8)$alkynyl, $CO_2R^{13}$, $SO_2R^{13}$, $C(O)NR^{13}R^{14}$, $SO_2NR^{13}R^{14}$ and $(C_1-C_4)$alkylene-$CO_2R^{13}$;

R'' is hydrogen or $(C_1-C_8)$alkyl;

each $R^1$ is independently selected from the group consisting of halogen, $(C_1-C_8)$alkyl, $(C_2-C_8)$alkenyl, $(C_2-C_8)$alkynyl, fluoro$(C_1-C_4)$alkyl, —$OR^5$, —$SR^5$, fluoro$(C_1-C_4)$alkoxy, aryl, aryl$(C_1-C_4)$alkyl, —$NO_2$, —$NR^5R^6$, —$C(O)R^5$, —$CO_2R^5$, —$C(O)NR^5R^6$, —$N(R^6)C(O)R^5$, —$N(R^6)CO_2R^5$, —$N(R^7)C(O)NR^5R^6$, —$S(O)_mNR^5R^6$, —$S(O)_mR^5$, —CN and —$N(R^6)S(O)_mR^5$;

$R^2$ is selected from the group consisting of halogen, $(C_1-C_8)$alkyl, $(C_2-C_8)$alkenyl, $(C_2-C_8)$alkynyl, fluoro$(C_1-C_4)$alkyl, —$OR^8$, —$SR^8$, fluoro$(C_1-C_4)$alkoxy, aryl, aryl$(C_1-C_4)$alkyl, —$NO_2$, —$NR^8R^9$, =O, —$C(O)R^8$, —$CO_2R^8$, —$C(O)NR^8R^9$, —$N(R^9)C(O)R^8$, —$N(R^9)CO_2R^8$, —$N(R^{10})C(O)NR^8R^9$, —$S(O)_mNR^8R^9$, —$S(O)_mR^8$, —CN and —$N(R^9)S(O)_mR^8$;

$R^4$ is selected from the group consisting of hydrogen —$OR^{11}$, —$C(O)R^{11}$, —$CO_2R^{11}$, —$C(O)NR^{11}R^{12}$, —CN, $(C_1-C_4)$alkyl and aryl;

$R^5$, $R^6$, $R^7$, $R^8$, $R^9$, $R^{10}$, $R^{11}$, $R^{12}$, $R^{13}$ and $R^{14}$ are independently selected from the group consisting of hydrogen, $(C_1-C_8)$alkyl, $(C_2-C_8)$alkenyl, $(C_2-C_8)$alkynyl, fluoro$(C_1-C_4)$alkyl, hetero$(C_1-C_4)$alkyl, aryl and aryl$(C_1-C_4)$alkyl;

optionally, when two R groups selected from the group consisting of $R^5$, $R^6$, $R^7$, $R^8$, $R^9$, $R^{10}$, $R^{11}$, $R^{12}$, $R^{13}$ and $R^{14}$ are attached to the same nitrogen atom, the R groups may be combined to form a 3-, 4-, 5-, 6- or 7-membered ring containing the nitrogen atom and from 0 to 2 additional heteroatoms selected from the group consisting of N, O and S;

the subscript m is 1 or 2; and the subscript n is 0, 1 or 2; and the subscript p is an integer of from 1 to 4.

Also provided herein are compounds of formula (III):

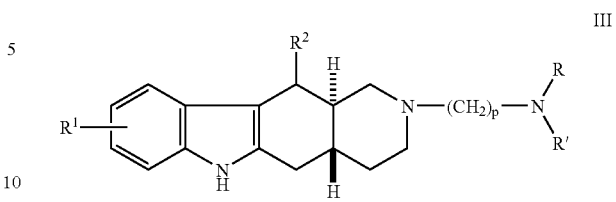

wherein

R and R' are independently selected from the group consisting of hydrogen, $(C_1-C_8)$alkyl, $(C_2-C_8)$alkenyl, $(C_2-C_8)$alkynyl, $CO_2R^{13}$, $SO_2R^{13}$, $C(O)NR^{13}R^{14}$, $SO_2NR^{13}R^{14}$ and $(C_1-C_4)$alkylene-$CO_2R^{13}$;

optionally, R and R' may be combined to form a 3-, 4-, 5-, 6- or 7-membered ring containing the nitrogen atom and from 0 to 2 additional heteroatoms selected from the group consisting of N, O and S;

R'' is hydrogen or $(C_1-C_8)$alkyl;

each $R^1$ is independently selected from the group consisting of halogen, $(C_1-C_8)$alkyl, $(C_2-C_8)$alkenyl, $(C_2-C_8)$alkynyl, fluoro$(C_1-C_4)$alkyl, —$OR^5$, —$SR^5$, fluoro$(C_1-C_4)$alkoxy, aryl, aryl$(C_1-C_4)$alkyl, —$NO_2$, —$NR^5R^6$, —$C(O)R^5$, —$CO_2R^5$, —$C(O)NR^5R^6$, —$N(R^6)C(O)R^5$, —$N(R^6)CO_2R^5$, —$N(R^7)C(O)NR^5R^6$, —$S(O)_mNR^5R^6$, —$S(O)_mR^5$, —CN and —$N(R^6)S(O)_mR^5$;

$R^2$ is selected from the group consisting of halogen, $(C_1-C_8)$alkyl, $(C_2-C_8)$alkenyl, $(C_2-C_8)$alkynyl, fluoro$(C_1-C_4)$alkyl, —$OR^8$, —$SR^8$, fluoro$(C_1-C_4)$alkoxy, aryl, aryl$(C_1-C_4)$alkyl, —$NO_2$, —$NR^8R^9$, =O, —$C(O)R^8$, —$CO_2R^8$, —$C(O)NR^8R^9$, —$N(R^9)C(O)R^8$, —$N(R^9)CO_2R^8$, —$N(R^{10})C(O)NR^8R^9$, —$S(O)_mNR^8R^9$, —$S(O)_mR^8$, —CN and —$N(R^9)S(O)_mR^8$;

$R^4$ is selected from the group consisting of hydrogen —$OR^{11}$, —$C(O)R^{11}$, —$CO_2R^{11}$, —$C(O)NR^{11}R^{12}$, —CN, $(C_1-C_4)$alkyl and aryl;

$R^5$, $R^6$, $R^7$, $R^8$, $R^9$, $R^{16}$ and $R^{17}$ are independently selected from the group consisting of hydrogen, $(C_1-C_8)$alkyl, $(C_2-C_8)$alkenyl, $(C_2-C_8)$alkynyl, fluoro$(C_1-C_4)$alkyl, hetero$(C_1-C_4)$alkyl, aryl and aryl$(C_1-C_4)$alkyl;

optionally, when two R groups selected from the group consisting of $R^5$, $R^6$, $R^7$, $R^8$, $R^9$, $R^{16}$ and $R^{17}$ are attached to the same nitrogen atom, the R groups may be combined to form a 3-, 4-, 5-, 6- or 7-membered ring containing the nitrogen atom and from 0 to 2 additional heteroatoms selected from the group consisting of N, O and S;

the subscript m is 1 or 2;

the subscript n is 0, 1 or 2; and the subscript p is an integer of from 1 to 4.

The compounds provided in the above formula are meant to include all pharmaceutically acceptable salts, hydrates, solvates or prodrugs thereof.

The pharmaceutical compositions provided herein comprise a pharmaceutically acceptable carrier or excipient in combination with a compound of formula I.

Methods for treating or preventing a condition or disorder selected from the group consisting of obesity, an eating disorder, an anxiety disorder and a mood disorder are provided herein. The methods comprise administering to a subject in need thereof a therapeutically effective amount of one of the foregoing compounds or pharmaceutical compositions.

Other objects, features and advantages of the present invention will become apparent to those skilled in the art from the following description and claims.

DETAILED DESCRIPTION OF THE INVENTION

Abbreviations and Definitions

Figure 1:
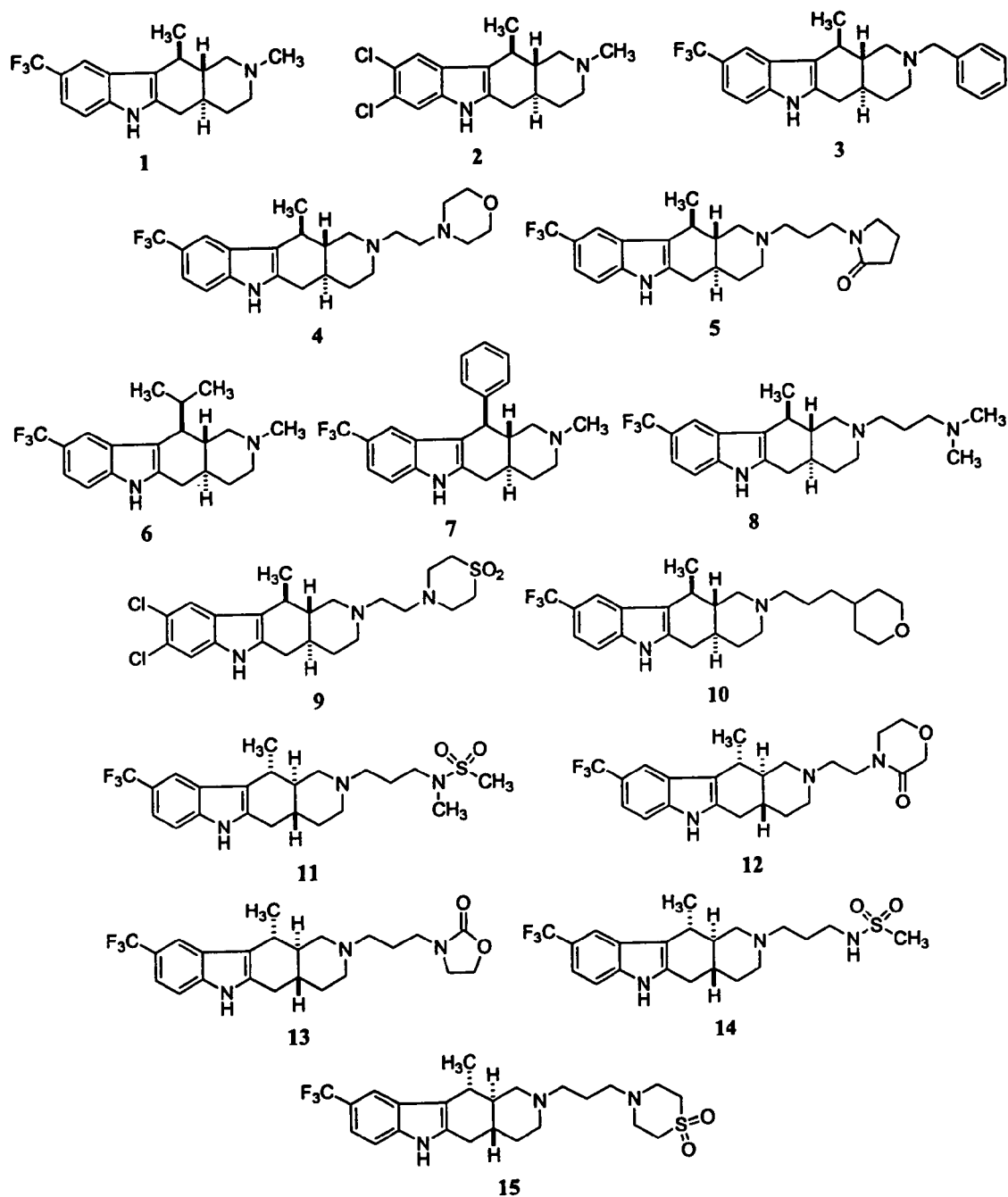
FIG. 1 provides the structures of exemplary compounds of the invention.
Figure 1B:
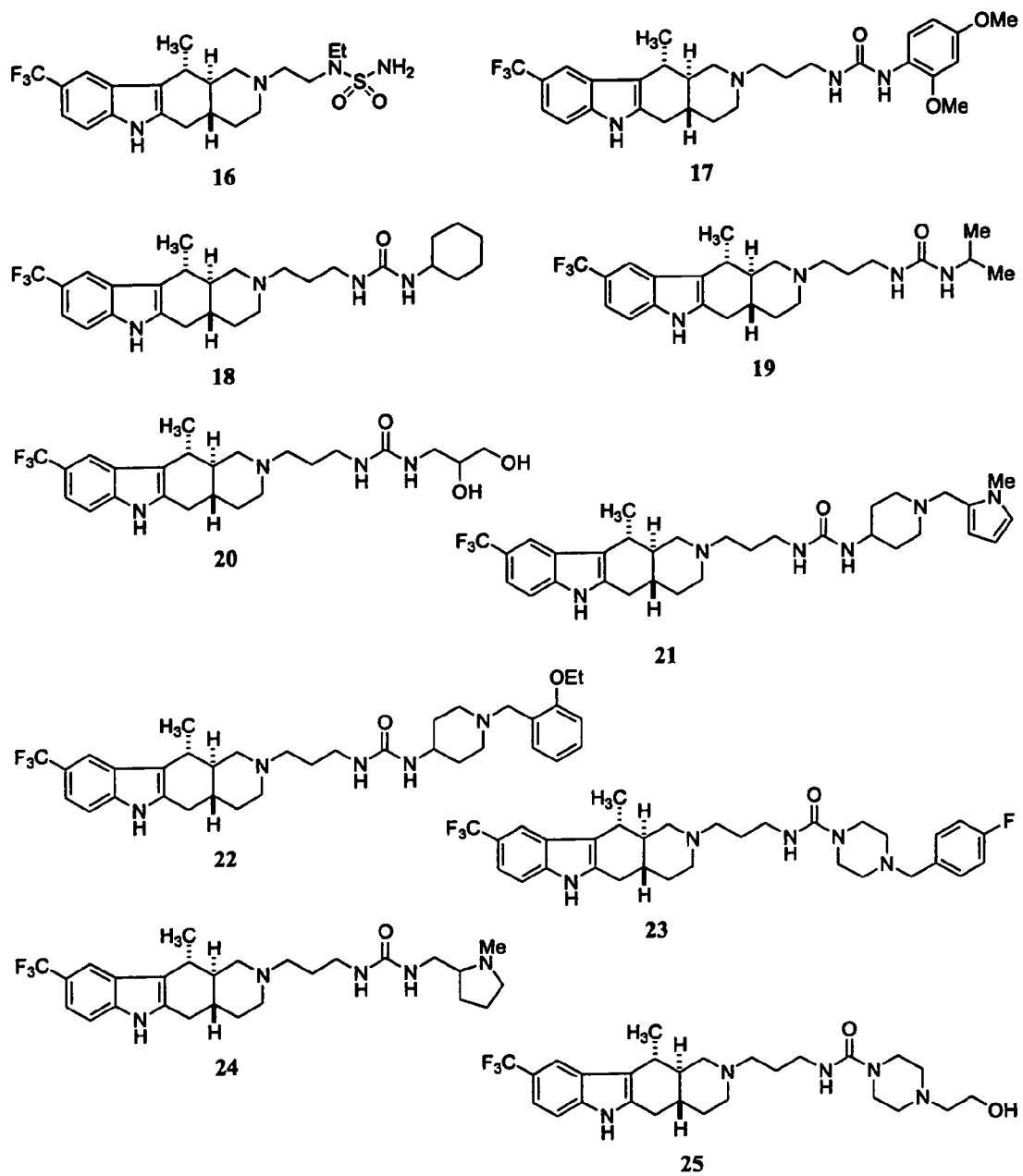

The abbreviations used herein are conventional, unless otherwise defined.

The term "MCHR" refers to the melanin-concentrating hormone receptor protein 1 (MCHR1), unless otherwise stated.

The terms "treat", "treating" and "treatment" refer to a method of alleviating or abrogating a disease and/or its attendant symptoms.

The terms "prevent", "preventing" and "prevention" refer to a method of decreasing the probability or eliminating the possibility that a disease will be contracted.

As used herein, the term "MCHR-mediated condition or disorder" and the like refers to a condition or disorder characterized by inappropriate, e.g., less than or greater than normal, MCHR activity. An MCHR-mediated condition or disorder may be completely or partially mediated by inappropriate MCHR activity. However, an MCHR-mediated condition or disorder is one in which modulation of MCHR results in some effect on the underlying condition or disease (e.g., an MCHR antagonist results in some improvement in patient well-being in at least some patients). Exemplary MCHR-mediated conditions and disorders include obesity, eating disorders and other behavioral disorders, such as anxiety disorders and mood disorders.

The term "therapeutically effective amount" refers to that amount of the compound being administered sufficient to prevent development of or alleviate to some extent one or more of the symptoms of the condition or disorder being treated.

As used herein, the term "obesity" refers to the excessive accumulation of body fat. Obesity may have genetic, environmental (e.g., expending less energy than is consumed) and regulatory determinants. Cardiovascular disorders, lipid disorders and metabolic disorders, such as hypertension, hyperlidemia, coronary artery disease and diabetes, are commonly associated with obesity.

As used herein, the terms "eating disorder", "feeding disorder", and the like refer to an emotional and/or behavioral disturbance associated with an excessive decrease in body weight and/or inappropriate efforts to avoid weight gain, e.g., fasting, self-induced vomiting, laxative or diuretic abuse. Depression is commonly associated with eating disorders. Exemplary eating disorders include anorexia nervosa and bulimia.

As used herein, the term "anxiety disorder" refers to an emotional and/or behavioral disturbance characterized by persistent and pervasive worry or restlessness, tension or irritability about, e.g., health, work, money or family, for no clear reason. An anxiety disorder may be accompanied by tachycardia or dyspnea. Exemplary anxiety disorders include anxiety, generalized anxiety disorder, panic attacks, panic disorder and obsessive-compulsive disorder (OCD).

As used herein, the term "mood disorder" refers to an emotional and/or behavioral disturbance characterized by persistent and pervasive bouts of euphoria and/or depression. Exemplary mood disorders include depression and bipolar disorders. Anxiety is frequently associated with mood disorders, such as depression.

The term "modulate" refers to the ability of a compound to increase or decrease the function, or activity, of MCHR. Modulation, as described herein, includes the antagonism or agonism of MCHR, either directly or indirectly. Antagonist are compounds that, e.g., partially or totally block stimulation, decrease, prevent, delay activation, inactivate, inhibit, desensitize, or down-regulate signal transduction. Agonists are compounds that, e.g., stimulate, increase, activate, open, facilitate, enhance activation, sensitize or up-regulate signal transduction.

The term "alkyl," by itself or as part of another substituent, means, unless otherwise stated, a straight or branched chain, or cyclic hydrocarbon radical, or combination thereof, which is fully saturated, having the number of carbon atoms designated (i.e. $C_1$–$C_8$ means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. As used herein, ($C_1$–$C_8$)alkyl refers to an alkyl group having from one to eight carbon atoms and includes, e.g., ($C_1$–$C_4$)alkyl.

The term "alkenyl", by itself or as part of another substituent, means a straight or branched chain, or cyclic hydrocarbon radical, or combination thereof, which may be mono- or polyunsaturated, having the number of carbon atoms designated (i.e. $C_2$–$C_8$ means two to eight carbons) and one or more double bonds. Examples of alkenyl groups include vinyl, allyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. $C_2$–$C_8$ means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having seven or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$ Similarly, the term "heteroalkylene" by itself or as part of another substituent means a divalent radical derived from heteroalkyl, as exemplified by —CH$_2$—CH$_2$—S—CH$_2$CH$_2$— and —CH$_2$—S—CH$_2$—CH$_2$—NH—CH$_2$—. For heteroalkylene groups, heteroatoms can also occupy either or both of the chain termini (e.g. alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., C$_3$–C$_8$ means three to eight carbons) and a heterocycloalkyl group consists of the number of atoms designated (i.e., C$_2$–C$_8$ means two to eight carbons) and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "halo(C$_1$–C$_4$)alkyl" is mean to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). Accordingly, the term "fluoro(C$_1$–C$_4$)alkyl" includes fluoromethyl, trifluoromethyl, 2,2,2-trifluoroethyl, pentafluoroethyl, 1,1-difluoroethyl, and the like. The term "perhaloalkyl" means, unless otherwise stated, alkyl substituted with (2m'+1) halogen atoms, where m' is the total number of carbon atoms in the alkyl group. For example the term "perhalo(C$_1$–C$_4$)alkyl" is meant to include trifluoromethyl, pentachloroethyl, 1,1,1-trifluoro-2-bromo-2-chloroethyl, and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl and 4-biphenyl.

The term "heteroaryl" refers to aryl groups (or rings) that contain from zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O; =NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR'—SO$_2$NR"R'", —NR"CO$_2$R', —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R, —CN and —NO$_2$, in a number ranging from zero to three, with those groups having zero, one or two substituents being particularly preferred. R', R" and R'" each independently refer to hydrogen, unsubstituted (C$_1$–C$_8$)alkyl and heteroalkyl, unsubstituted aryl, aryl substituted with one to three halogens, unsubstituted alkyl, alkoxy or thioalkoxy groups, or aryl(C$_1$–C$_4$)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the present invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR', halogen, —SiR'R"R'", —OC(O)R', —C(O)R', —CO$_2$R', —CONR'R", —OC(O)NR'R", —NR"C(O)R', —NR"CO$_2$R', —NR'—SO$_2$NR"R'", —S(O)R', —SO$_2$R', —SO$_2$NR'R", —NR"SO$_2$R, —CN and —NO$_2$, where R' and R'' are as defined above. Further preferred substituents are selected from: —OR', =O, —NR'R'', halogen, —OC(O)R', —CO$_2$R', —CONR'R'', —OC(O)NR'R'', —NR''C(O)R', —NR''CO$_2$R', —NR'—SO$_2$NR''R''', —SO$_2$R', —SO$_2$NR'R'', —NR''SO$_2$R, —CN and —NO$_2$ Similarly, substituents for the aryl and heteroaryl groups are varied and selected from: halogen, —OR', —OC(O)R', —NR'R'', —SR', —R', —CN, —NO$_2$, —CO$_2$R', —CONR'R'', —C(O)R', —OC(O)NR'R'', —NR''C(O)R', —NR''CO$_2$R', —NR'—C(O)NR''R''', —NR'—SO$_2$NR''R''', —NH—C(NH$_2$)=NH, —NR'C(NH$_2$)=NH, —NH—C(NH$_2$)=NR', —S(O)R', —SO$_2$R', —SO$_2$NR'R'', —NR''SO$_2$R, —N$_3$, —CH(Ph)$_2$, perfluoro(C$_1$–C$_4$)alkoxy and perfluoro(C$_1$–C$_4$)alkyl, in a number ranging from zero to the total number of open valences on the aromatic ring system; and where R', R'' and R''' are independently selected from hydrogen, (C$_1$–C$_8$)alkyl and heteroalkyl, unsubstituted aryl and heteroaryl, (unsubstituted aryl)-(C$_1$–C$_4$)alkyl and (unsubstituted aryl)oxy-(C$_1$–C$_4$)alkyl. Typically, an aryl or heteroaryl group will have from zero to three substituents, with those groups having two or fewer substituents being preferred in the present invention. More preferably, an aryl or heteroaryl group will be unsubstituted or monosubstituted. Most preferably, an aryl or heteroaryl group will be unsubstituted.

Preferred substituents for aryl and heteroaryl groups are selected from: halogen, —OR', —OC(O)R', —NR'R'', —SR', —R', —CN, —NO$_2$, —CO$_2$R', —CONR'R'', —C(O)R', —OC(O)NR'R'', —NR''C(O)R', —S(O)R', —SO$_2$R', —SO$_2$NR'R'', —NR''SO$_2$R, —N$_3$, —CH(Ph)$_2$, perfluoro(C$_1$–C$_4$)alkoxy and perfluoro(C$_1$–C$_4$)alkyl, where R' and R'' are as defined above. Further preferred substituents are selected from: halogen, —OR', —OC(O)R', —NR'R'', —R', —CN, —NO$_2$, —CO$_2$R', —CONR'R'', —NR''C(O)R', —SO$_2$R', —SO$_2$NR'R'', —NR''SO$_2$R, perfluoro(C$_1$–C$_4$)alkoxy and perfluoro(C$_1$–C$_4$)alkyl As used herein, the substituent CO$_2$H, includes bioisosteric replacements therefor, such as:

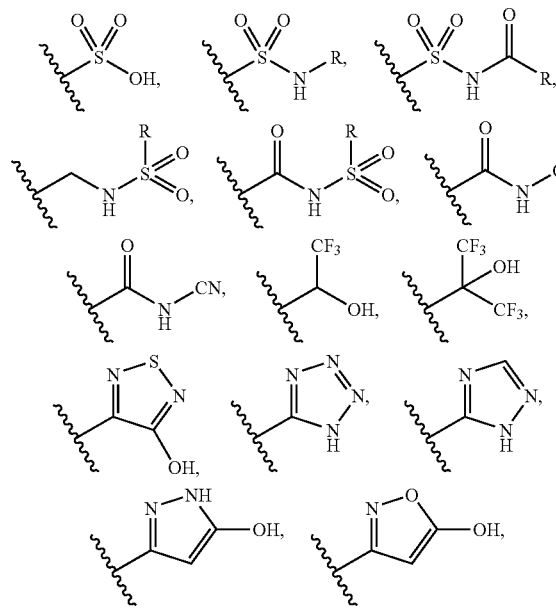

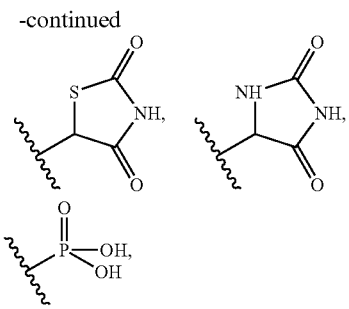

and the like. See, e.g., *The Practice of Medicinal Chemistry;* Wermuth, C. G., Ed.; Academic Press: New York, 1996; p. 203.

Two of the substituents on adjacent atoms of the aryl ring may optionally be replaced with a substituent of the formula -T-C(O)—(CH$_2$)$_q$—U— wherein T and U are independently —NH—, —O—, —CH$_2$— or a single bond, and q is an integer of from 0 to 2. Alternatively, two of the substituents on adjacent atoms of the aryl ring may optionally be replaced with a substituent of the formula —A—(CH$_2$)$_r$—B—, wherein A and B are independently —CH$_2$—, —O—, —NH—, —S—, —S(O)—, —SO$_2$—, —SO$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —SO$_2$—, or —SO$_2$NR'—. The substituent R' in —NR'— and —SO$_2$NR'— is selected from the group consisting of hydrogen or unsubstituted (C$_1$–C$_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al. (1977) *J. Pharm. Sci.* 66:1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, enantiomers, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

EMBODIMENTS OF THE INVENTION

MCHR (GenBank Accession No. U71092) is expressed in brain, at moderate levels in the eye and skeletal muscle, and in low levels in tongue and the pituitary gland. Evidence suggests that MCHR is involved in, inter alia, olfactory learning, regulation of feeding behavior and energy metabolism, regulation of the hypothalmic-pituitary-adrenocortical axis following stress, arousal and the sensation of anxiety (Saito et al., *TEM* 11(8):299–303 (2000)). The compounds of the present invention inhibit MCHR activity, and thus, are useful in, for example, the treatment or prevention of disorders associated with these processes.

Compounds

In one aspect, the present invention provides compounds represented by the formula (I):

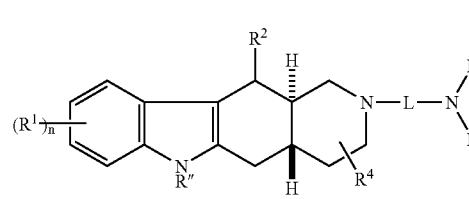

or a pharmaceutically acceptable salt, hydrate, solvate or prodrug thereof. In formula I, the symbol L represents a divalent linkage selected from a bond and ($C_1$–$C_4$)alkylene. Exemplary L groups are a single bond, methylene, ethylene, n-propylene and n-butylene.

R and R' are independently selected from hydrogen, ($C_1$–$C_8$)alkyl, ($C_2$–$C_8$)alkenyl, ($C_2$–$C_8$)alkynyl, $CO_2R^{13}$, $SO_2R^{13}$, $C(O)NR^{13}R^{14}$, $SO_2NR^{13}R^{14}$ and ($C_1$–$C_4$)alkylene-$CO_2R^{13}$. Optionally, R and R' may be combined to form a 3-, 4-, 5-, 6- or 7-membered ring containing the nitrogen atom and from 0 to 2 additional heteroatoms selected from N, O and S. Exemplary NRR' groups are:

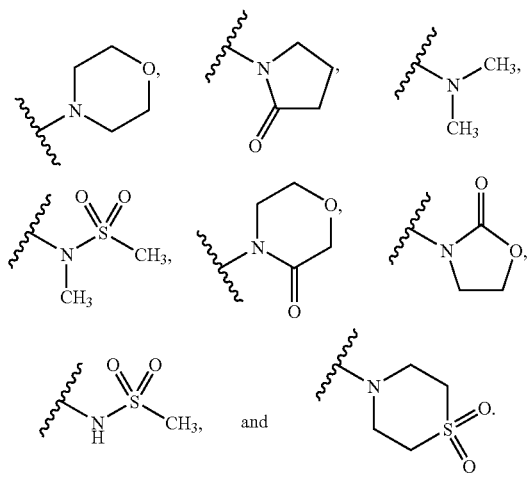

R" is hydrogen or ($C_1$–$C_8$)alkyl.

Each $R^1$ is independently halogen, ($C_1$–$C_8$)alkyl, ($C_2$–$C_8$)alkenyl, ($C_2$–$C_8$)alkynyl, fluoro($C_1$–$C_4$)alkyl, —$OR^5$, —$SR^5$, fluoro($C_1$–$C_4$)alkoxy, aryl, aryl($C_1$–$C_4$)alkyl, —$NO_2$, —$NR^5R^6$, —$C(O)R^5$, —$CO_2R^5$, —$C(O)NR^5R^6$, —$N(R^6)C(O)R^5$, —$N(R^6)CO_2R^5$, —$N(R^7)C(O)NR^5R^6$, —$S(O)_mNR^5R^6$, —$S(O)_mR^5$, —CN or —$N(R^6)S(O)_mR^5$. Exemplary $R^1$ groups are Cl and $CF_3$.

$R^2$ is selected from halogen, ($C_1$–$C_8$)alkyl, ($C_2$–$C_8$)alkenyl, ($C_2$–$C_8$)alkynyl, fluoro($C_1$–$C_4$)alkyl, —$OR^8$, —$SR^8$, fluoro($C_1$–$C_4$)alkoxy, aryl, aryl($C_1$–$C_4$)alkyl, —$NO_2$, —NR$^8$R$^9$, =O, —C(O)R$^8$, —CO$_2$R$^8$, —C(O)NR$^8$R$^9$, —N(R$^9$)C(O)R$^8$, —N(R$^9$)CO$_2$R$^8$, —N(R$^{10}$)C(O)NR$^8$R$^9$, —S(O)$_m$R$^8$R$^9$, —S(O)$_m$R$^8$, —CN and —N(R$^9$)S(O)$_m$R$^8$. Exemplary R$^2$ groups are methyl, isopropyl, trifluoromethyl, hydroxy, methoxy, hydroxymethyl, trifluoromethoxy, phenyl and =O.

R$^4$ is hydrogen —OR$^{11}$, —C(O)R$^{11}$, —CO$_2$R$^{11}$, —C(O)NR$^{11}$R$^{12}$, —CN, (C$_1$–C$_4$)alkyl or aryl.

R$^5$, R$^6$, R$^7$, R$^8$, R$^9$, R$^{10}$, R$^{11}$, R$^{12}$, R$^{13}$, R$^{14}$, R$^{16}$ and R$^{17}$ are independently selected from hydrogen, (C$_1$–C$_8$)alkyl, (C$_2$–C$_8$)alkenyl, (C$_2$–C$_8$)alkynyl, fluoro(C$_1$–C$_4$)alkyl, hetero(C$_1$–C$_4$)alkyl, aryl and aryl(C$_1$–C$_4$)alkyl. The subscript m is 1 or 2 and the subscript n is 0, 1 or 2. Optionally, when two R groups selected from the group consisting of R$^5$, R$^6$, R$^7$, R$^8$, R$^9$, R$^{10}$, R$^{11}$, R$^{12}$, R$^{13}$ and R$^{14}$ are attached to the same nitrogen atom, the R groups may be combined to form a 3-, 4-, 5-, 6- or 7-membered ring containing the nitrogen atom and from 0 to 2 additional heteroatoms selected from N, O and S.

The compounds of the invention feature a pyrido[4,3-b] carbazole-derived ring, minimally substituted at the 2- and 11-positions. The ring numbering system used herein is illustrated below.

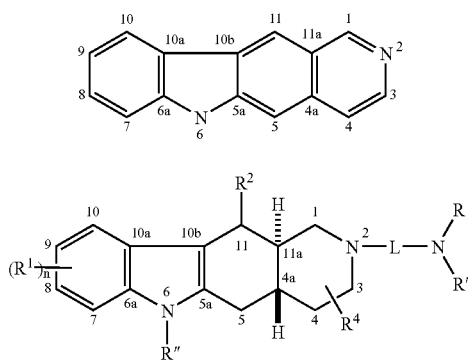

One of skill in the art will understand that formula I encompasses two enantiomers. The enantiomers have the structural orientations represented by the following formulae:

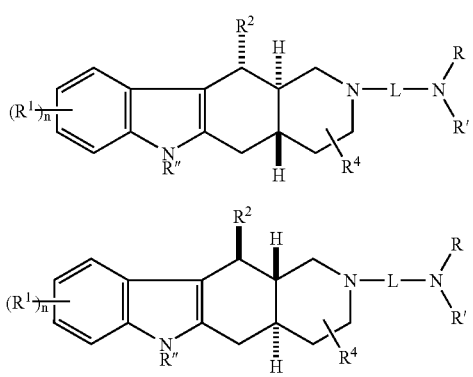

Within formula I above, a number of groups of embodiments are preferred, described below.

In one group of preferred embodiments, L is (C$_1$–C$_4$) alkylene. In a preferred embodiment, L is unsubstituted (C$_1$–C$_4$)alkylene or (CH$_2$)$_p$, wherein the subscript p is an integer of from 1 to 4. In a further preferred embodiment, p is 1, 2 or 3. In a still further preferred embodiment, p is 2 or 3.

One group of preferred embodiments is represented by the formula (II):

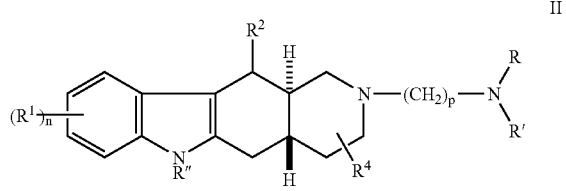

wherein L is (C$_1$–C$_4$)alkylene.

In a preferred embodiment, R and R' are combined to form a 3-, 4-, 5-, 6- or 7-membered ring containing nitrogen and from 0 to 2 additional heteroatoms selected from O, N and S. In a further preferred embodiment, R and R' are combined to form a 5- or 6-membered ring containing nitrogen and from 0 to 2 additional heteroatoms selected from O, N and S.

In another group of preferred embodiments, R" is hydrogen.

In another group of preferred embodiments, R" is substituted (C$_1$–C$_8$)alkyl. In a preferred embodiment, R" is (C$_1$–C$_8$)alkyl substituted with hydroxy, alkylamino (e.g., NHMe) or carboxy (CO$_2$H). In a particularly preferred embodiment, R" is (C$_3$–C$_8$)alkyl substituted with hydroxy, alkylamino or carboxy.

In another group of preferred embodiments, R$^1$ is independently halogen, (C$_1$–C$_4$)alkyl, fluoro(C$_1$–C$_4$)alkyl, —OR$^5$, fluoro(C$_1$–C$_4$)alkoxy, —CO$_2$R$^5$, —S(O)$_m$NR$^5$R$^6$, —S(O)$_m$R$^5$ or —CN. In a further preferred embodiment, R$^1$ is independently halogen or fluoro(C$_1$–C$_4$)alkyl. In a still further preferred embodiment, R$^1$ is halogen or fluoro (C$_1$–C$_4$)alkyl and the subscript n is 0 or 1. In a particularly preferred embodiment, R$^1$ is fluoro(C$_1$–C$_4$)alkyl and the subscript n is 0 or 1.

In another group of preferred embodiments, R$^2$ is (C$_1$–C$_4$) alkyl or aryl.

In another group of preferred embodiments, R$^4$ is hydrogen.

Also particularly preferred are those embodiments that combine two or more of these preferred groups. Accordingly, in one group of particularly preferred embodiments, R" and R$^4$ are hydrogen.

In another group of particularly preferred embodiments, R" and R$^4$ are hydrogen and R$^2$ is (C$_1$–C$_4$)alkyl or aryl.

In another group of particularly preferred embodiments, R" and R$^4$ are hydrogen, R$^1$ is independently halogen, (C$_1$–C$_4$)alkyl, fluoro(C$_1$–C$_4$)alkyl, —OR$^5$, fluoro(C$_1$–C$_4$) alkoxy, —CO$_2$R$^5$, S(O)$_m$NR$^5$R$^6$, —S(O)$_m$R$^5$ or —CN and R$^2$ is (C$_1$–C$_4$)alkyl or aryl. In a particularly preferred embodiment, R" and R$^4$ are hydrogen, R$^1$ is halogen or fluoro(C$_1$–C$_4$)alkyl, n is 1 and R$^2$ is (C$_1$–C$_4$)alkyl or aryl. In a more particularly preferred embodiment, R" and R$^4$ are hydrogen, R' is fluoro(C$_1$–C$_4$)alkyl, n is 1 and R$^2$ is (C$_1$–C$_4$) alkyl or aryl.

In another particularly preferred embodiment embodiment, R$^1$ is independently halogen, (C$_1$–C$_4$)alkyl, fluoro (C$_1$–C$_4$)alkyl, —OR$^5$, fluoro(C$_1$–C$_4$)alkoxy, —CO$_2$R$^5$, —S(O)$_m$NR$^5$R$^6$, —S(O)$_m$R$^5$ or —CN and R$^2$ is (C$_1$–C$_4$) alkyl or aryl.

In another particularly preferred embodiment embodiment, $R^1$ is independently halogen, $(C_1-C_4)$alkyl, fluoro$(C_1-C_4)$alkyl, —$OR^5$, fluoro$(C_1-C_4)$alkoxy, —$CO_2R^5$, —$S(O)_mNR^5R^6$, —$S(O)_mR^5$ or —CN.

In another particularly preferred embodiment embodiment, $R^2$ is $(C_1-C_4)$alkyl or aryl.

In another particularly preferred embodiment embodiment, $R^1$ is independently halogen, $(C_1-C_4)$alkyl, fluoro$(C_1-C_4)$alkyl, —$OR^5$, fluoro$(C_1-C_4)$alkoxy, —$CO_2R^5$, —$S(O)_mNR^5R^6$, —$S(O)_mR^5$ or —CN, $R^2$ is $(C_1-C_4)$alkyl or aryl.

Another group of particularly preferred embodiments is represented by the formula (III):

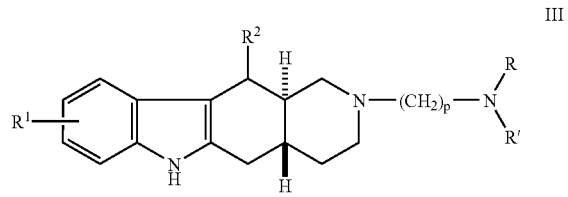

III wherein p, $R^1$, $R^2$, R and R' have the meanings and preferred groupings provided above.

In a particularly preferred embodiment embodiment, $R^1$ is independently halogen, $(C_1-C_4)$alkyl, fluoro$(C_1-C_4)$alkyl, —$OR^5$, fluoro$(C_1-C_4)$alkoxy, —$CO_2R^5$, —$S(O)_mNR^5R^6$, —$S(O)_nR^5$ or —CN and $R^2$ is $(C_1-C_4)$alkyl or aryl.

Compositions

In another aspect, the present invention provides pharmaceutical compositions comprising one or more compounds of the invention in combination with a diagnostically or pharmaceutically acceptable carrier or excipient. The subject compositions are useful for treating or preventing conditions and disorders mediated by MCHR, such as obesity and eating disorders, e.g., anorexia nervosa. The compounds of the present invention can be prepared and administered in a wide variety of oral and parenteral dosage forms. Thus, the compounds of the present invention can be administered by injection, for example, intravenously, intramuscularly, intracutaneously, subcutaneously, intraduodenally or intraperitoneally. Also, the compounds described herein can be administered by inhalation, for example, intranasally. Additionally, the compounds of the present invention can be administered transdermally. Other routes of administration are also contemplated for use with the compounds of the present invention, including depot administration and rectal administration.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders and tablets preferably contain from about 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg according to the particular application and the potency of the active component. The composition can, if desired, also contain other compatible therapeutic agents.

In therapeutic use for the treatment or prevention of conditions and disorders associated with MCHR, the compounds utilized in the pharmaceutical method of the invention are administered at the initial dosage of about 0.001 mg/kg to about 100 mg/kg daily. A daily dose range of about 0.1 mg/kg to about 10 mg/kg is preferred. The dosages, however, may be varied depending upon the requirements of the patient, the severity of the condition being treated and the compound being employed. Determination of the proper dosage for a particular situation is within the skill of the practitioner. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The compositions may be advantageously combined and/or used in combination with agents useful in the treatment and/or prevention of obesity and eating disorders and pathologies associated therewith (e.g., cardiovascular disease and hypertension). In many instances, administration of the subject compounds or compositions in conjunction with these alternative agents enhances the efficacy of such agents. Accordingly, in some instances, the present compounds, when combined or administered in combination with, e.g., anti-obesity agents, can be used in dosages which are less than the expected amounts when used alone, or less than the calculated amounts for combination therapy.

Suitable agents for combination therapy include those that are currently commercially available and those that are in development or will be developed. Exemplary agents useful in the treatment of obesity include $\beta_3$ adrenergic receptor agonists, leptin or derivatives thereof and neuropeptide Y antagonists. Exemplary agents useful in the treatment of anxiety and/or mood disorders include benzodiazepines, e.g., alprazolam, chlordiazepoxide, clonazepam, clorazepate, diazepam, lorazepam, oxazepam, and the like; heterocyclic antidepressants, e.g, amitriptyline, nortriptyline, imipramine, desipramine, doxepin, trimipramine, clomipramine, protryptyline, amoxapine and maprotiline; monoamine oxidase inhibitors (MAOIs), e.g., phenelzine and tranylcypromine; serotonin reuptake inhibitors (SRIs); selective serotonin reuptake inhibitors (SSRIs), e.g., fluoxetine, fluvoxamine, paroxetine and sertraline; serotonergic-noradrenergic antidepressants, e.g., venlafaxine; 5-HT2 antagonists, e.g., trazadone, nefazodone and mirtazapine; and catecholaminergic antidepressants, e.g., buproprion.

Methods of Use

In yet another aspect, the present invention provides methods of using one or more compounds of the invention to treat or prevent a condition or disorder associated with eating behavior, energy homeostasis or anxiety. Exemplary conditions and disorders associated with eating behavior, energy homeostasis and anxiety include eating disorders, such as anorexia nervosa and bulimia, obesity, anxiety disorders, e.g., generalized anxiety disorder, panic attacks, panic disorder and obsessive-compulsive disorder (OCD), and mood disorders, e.g., depression and bipolar disorders. Methods of using a compound of the invention to treat or prevent a condition or disorder associated with eating behavior include methods of modifying eating behavior or food intake, for example, stimulating or suppressing eating behavior or increasing or decreasing food intake. The methods comprise administering to a subject in need thereof a therapeutically effective amount of a compound of the invention.

In another aspect, the present invention provides methods of using a compound of the invention to treat or prevent a condition or disorder mediated by MCHR. The methods comprise administering to a subject in need thereof a therapeutically effective amount of a compound of the invention.

In still another aspect, the present invention provides methods of using a compound of the invention to modulate MCHR. The methods comprise contacting a cell with a compound of the invention.

The compounds of the invention may also modulate G-protein coupled receptors related to MCHR, e.g., MCHR2 (see International Publication Nos. WO 00/49046 and WO 01/07606).

Preparation of the Compounds

The present invention provides a process for the preparation of a compound of formula I.

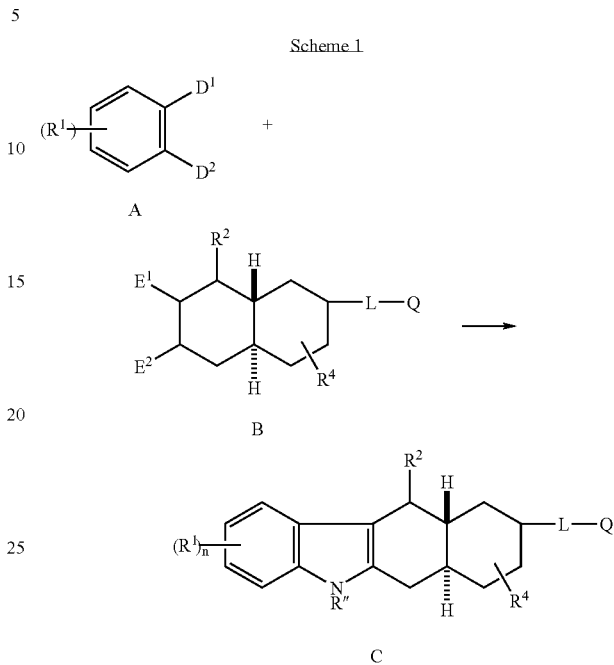

Scheme 1

A general synthetic route is depicted in Scheme 1, which outlines the condensation of substituted aryl moiety A, with a bicyclic structure B to produce a compound of formula C, wherein Q represents NRR' and the remaining variables are defined as above. In formula A, $D^1$ is hydrogen and $D^2$ is —NH—NH$_2$ or a protected version thereof Conventional amino protecting groups consist of known groups which are used to protectively block an amino group during the synthesis procedures described herein. These conventional blocking groups are readily removable, i.e., they can be removed, if desired, by procedures which will not cause cleavage or other disruption of the remaining portions of the molecule. Suitable protecting groups for the compounds of the present invention will be recognized from the present application taking into account the level of skill in the art, and with reference to standard textbooks, such as Greene, T. W. et al, *Protective Groups in Organic Synthesis,* Wiley, New York (1991).

In formula B, $E^1$ is hydrogen. When a compound of formula A, wherein $D^1$ is hydrogen, reacts with a compound of formula B, wherein E2 is =O or a protected version thereof, under the typical Fisher indolization conditions, a compound of formula C is produced.

One of skill in the art will understand that the synthesis provided above can be modified to use different starting materials and alternate reagents to accomplish the desired transformations. For example, a compound of formula A, wherein $D^1$ is a leaving group such as Cl, Br, I or toluenesulfonate, can react with a compound of formula B, wherein $E^2$ is =O or a protected version thereof, via a palladium-catalyzed coupling reaction to produce a compound of formula C. Also, a compound of formula A, wherein $D^1$ is a leaving group and $D^2$ is a nitro group, can react with a compound of formula B, wherein $E^1$ is CO$_2$R and wherein $E^2$ is =O or a protected version thereof, to produce a compound of formula C. Accordingly, the synthesis and reagents described herein are all expressed as non-limiting embodiments.

Materials represented by formula A are available commercially (Aldrich Chemical), or can be obtained synthetically following literature procedures.

One way to prepare compounds represented by formula B is by the Robinson annulation process between a cyclic ketone and a substituted enone followed by saturation of the double bond. One of the skill in the art will readily appreciate that other methods are available. The relative stereochemistry and absolute stereochemistry can be controlled in the process. The individual forms of compounds of formula B, e.g., diastereomers and enantiomers, can be formed by stereocontrolled reactions, or may be separated, e.g., by chromatographic techniques (diastereomers) and by resolution (enantiomers).

Analysis of the Compounds

The activity of MCHR polypeptides can be assessed using a variety of in vitro and in vivo assays to determine functional, chemical and physical effects, e.g., measuring ligand binding (e.g., radioactive ligand binding), second messenger (e.g., cAMP, cGMP, $IP_3$, DAG, or $Ca^{2+}$) levels, ion flux, phosphorylation levels, transcription levels, neurotransmitter levels, and the like. Furthermore, such assays can be used to test for antagonists and agonists of MCHR. Screening assays may be used to identify modulators that can be used as therapeutic agents, e.g., antagonists of MCHR activity.

Modulators of MCHR activity can be tested using MCHR polypeptides as described above, either recombinant or naturally occurring (e.g., endogenous). The protein can be isolated, expressed in a cell, expressed in a membrane derived from a cell, expressed in tissue or in an animal, either recombinant or naturally occurring. For example, kidney cells, liver cells, colon cells, transformed cells, or membranes can be used. Modulation is tested using one of the in vitro or in vivo assays described herein. Signal transduction can also be examined in vitro with soluble or solid state reactions, using a chimeric molecule such as an extracellular domain of a receptor covalently linked to a heterologous signal transduction domain, or a heterologous extracellular domain covalently linked to the transmembrane and or cytoplasmic domain of a receptor. Gene amplification can also be examined. Furthermore, ligand-binding domains of the protein of interest can be used in vitro in soluble or solid state reactions to assay for ligand binding.

Ligand binding to MCHR, a domain, or chimeric protein can be tested in solution, in a bilayer membrane, attached to a solid phase, in a lipid monolayer, or in vesicles. Binding of a modulator can be tested using, e.g., changes in spectroscopic characteristics (e.g., fluorescence, absorbance, refractive index) hydrodynamic (e.g., shape), chromatographic, or solubility properties.

MCHR-G-protein interactions can also be examined, by, for example, analysis of binding of the G-protein to MCHR or its release from MCHR can be examined. For example, in the absence of GTP, an activator will lead to the formation of a tight complex of a G protein (all three subunits) with MCHR. This complex can be detected in a variety of ways, as noted above. Such an assay can be modified to search for antagonists. In one embodiment, an activator is added to MCHR and G protein in the absence of GTP, allowed to form a tight complex, and then screened for antagonists by looking at dissociation of the MCHR-G protein complex. In the presence of GTP, release of the alpha subunit of the G protein from the other two G protein subunits serves as a criterion of activation.

An activated or inhibited G-protein will in turn alter the properties of downstream effectors such as proteins, enzymes and channels. The classic examples are the activation of cGMP phosphodiesterase by transducin in the visual system, adenylate cyclase by the stimulatory G-protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

Activated MCHR becomes a substrate for kinases that phosphorylate the C-terminal tail of the receptor (and possibly other sites as well). Thus, activators will promote the transfer of $^{32}P$ from gamma-labeled ATP to the receptor, which can be assayed with a scintillation counter. The phosphorylation of the C-terminal tail will promote the binding of arrestin-like proteins and will interfere with the binding of G-proteins. The kinase/arrestin pathway plays a key role in the desensitization of many GPCR receptors. For a general review of GPCR signal transduction and methods of assaying signal transduction, see, e.g., *Methods in Enzymology*, vols. 237 and 238 (1994) and volume 96 (1983); Bourne et al., *Nature* 10:349:117–27 (1991); Bourne et al., *Nature* 348:125–32 (1990); Pitcher et al., *Annu. Rev. Biochem.* 67:653–92 (1998).

Samples or assays that are treated with a potential MCHR antagonist or agonist are compared to control samples without the test compound, to examine the extent of modulation. Control samples (untreated with agonists or antagonist) are assigned a relative MCHR activity value of 100. Inhibition of MCHR is achieved when the MCHR activity value relative to the control is about 90%, optionally 50%, optionally 25–0%. Activation of MCHR is achieved when the MCHR activity value relative to the control is 110%, optionally 150%, 200–500%, or 1000–2000%.

Changes in ion flux may be assessed by determining changes in polarization (ie., electrical potential) of the cell or membrane expressing MCHR. One means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336:1575–1595 (1997)). Whole cell currents are conveniently determined using the standard methodology (see, e.g., Hamil et al., *PFlugers. Archiv.* 391:85 (1981). Other known assays include radiolabeled ion flux assays and fluorescence assays using voltage-sensitive dyes (see, e.g., Vestergarrd-Bogind et al., *J. Membrane Biol.* 88:67–75 (1988); Gonzales & Tsien, *Chem. Biol.* 4:269–277 (1997); Daniel et al., *J. Pharmacol. Meth.* 25:185–193 (1991); Holevinsky et al., *J. Membrane Biology* 137:59–70 (1994)). Generally, the compounds to be tested are present in the range from 1 pM to 100 mM.

The effects of the test compounds upon the function of the polypeptides can be measured by examining any of the parameters described above. Any suitable physiological change that affects MCHR activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, IP3 or cAMP.

Preferred assays for MCHR include cells that are loaded with ion- or voltage-sensitive dyes to report receptor activity. Assays for determining activity of such receptors can also use known agonists and antagonists for other G-protein coupled receptors as negative or positive controls to assess activity of tested compounds. In assays for identifying modulatory compounds (e.g., agonists, antagonists), changes in the level of ions in the cytoplasm or membrane voltage will be monitored using an ion-sensitive or membrane voltage fluorescent indicator, respectively. Among the ion-sensitive indicators and voltage probes that may be employed are those disclosed in the Molecular Probes 1997 Catalog. For G-protein coupled receptors, promiscuous G-proteins such as Gα15 and Gα16 can be used in the assay of choice (Wilkie et al., *Proc. Natl Acad. Sci. USA* 88:10049–10053 (1991)). Such promiscuous G-proteins allow coupling of a wide range of receptors to signal transduction pathways in heterologous cells.

Receptor activation typically initiates subsequent intracellular events, e.g., increases in second messengers such as IP3, which releases intracellular stores of calcium ions. Activation of some G-protein coupled receptors stimulates the formation of inositol triphosphate (IP3) through phospholipase C-mediated hydrolysis of phosphatidylinositol (Berridge & Irvine, *Nature* 312:315–21 (1984)). IP3 in turn stimulates the release of intracellular calcium ion stores. Thus, a change in cytoplasmic calcium ion levels, or a change in second messenger levels such as IP3 can be used to assess G-protein coupled receptor function. Cells expressing such G-protein coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

Other assays can involve determining the activity of receptors which, when activated, result in a change in the level of intracellular cyclic nucleotides, e.g., cAMP or cGMP, by activating or inhibiting downstream effectors such as adenylate cyclase. There are cyclic nucleotide-gated ion channels, e.g., rod photoreceptor cell channels and olfactory neuron channels that are permeable to cations upon activation by binding of cAMP or cGMP (see, e.g., Altenhofen et al., *Proc. Natl. Acad. Sci. U.S.A.* 88:9868–9872 (1991) and Dhallan et al., *Nature* 347:184–187 (1990)). In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-gated ion channel, GPCR phosphatase and DNA encoding a receptor (e.g., certain glutamate receptors, muscarinic acetylcholine receptors, dopamine receptors, serotonin receptors, and the like), which, when activated, causes a change in cyclic nucleotide levels in the cytoplasm.

In one embodiment, changes in intracellular cAMP or cGMP can be measured using immunoassays. The method described in Offermanns & Simon, *J. Biol. Chem.* 270: 15175–15180 (1995) may be used to determine the level of cAMP. Also, the method described in Felley-Bosco et al., *Am. J. Resp. Cell and Mol. Biol.* 11:159–164 (1994) may be used to determine the level of cGMP. Further, an assay kit for measuring cAMP and/or cGMP is described in U.S. Pat. No. 4,115,538, herein incorporated by reference. In another embodiment, phosphatidyl inositol (PI) hydrolysis can be analyzed according to U.S. Pat. No. 5,436,128, herein incorporated by reference.

In another embodiment, transcription levels can be measured to assess the effects of a test compound on signal transduction. A host cell containing the protein of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using a reporter gene may be used as described in U.S. Pat. No. 5,436,128, herein incorporated by reference. The reporter genes can be, e.g., chloramphenicol acetyltransferase, firefly luciferase, bacterial luciferase, β-galactosidase and alkaline phosphatase. Furthermore, the protein of interest can be used as an indirect reporter via attachment to a second reporter such as green fluorescent protein (see, e.g., Mistili & Spector, *Nature Biotechnology* 15:961–964 (1997)).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant (or non-recombinant) cell line was prepared but which had not been modified by introduction of heterologous DNA. Any difference in the amount of transcription indicates that the test compound has in some manner altered the activity of the protein of interest.

The following examples are provided by way of illustration only and not by way of limitation. Those of skill in the art will readily recognize a variety of noncritical parameters that could be changed or modified to yield essentially similar results.

EXAMPLES

Reagents and solvents used below can be obtained from commercial sources such as Aldrich Chemical Co. (Milwaukee, Wis., USA). $^1$H-NMR spectra were recorded on a Varian Gemini 400 MHz NMR spectrometer. Significant peaks are tabulated in the order: multiplicity (s, singlet; d, doublet; t, triplet; q, quartet; m, multiplet; br s, broad singlet), coupling constant(s) in Hertz (Hz) and number of protons. Electron Ionization (EI) mass spectra were recorded on a Hewlett Packard 5989A mass spectrometer. Mass spectrometry results are reported as the ratio of mass over charge, followed by the relative abundance of each ion (in parentheses). A single m/e value is reported for the M+H (or, as noted, M–H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1 100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2 mM NH$_4$OAc in acetonitrile/water as delivery solvent. Analytical HPLC analysis was conducted on a Hewlett-Packard Series 1050 system equipped with a C18 reverse phase column (4.6 mm×—150 mm) manufactured by Shiseido Co., Japan. Gradient elution was performed using variable percentage of acetonitrile and water (each with 0.1% trifluoroacetic acid added) as a mobile phase. Optical purity analysis was also conducted on a Hewlett-Packard Series 1050 system equipped with a chiral HLPC column (ChiralPak AD, 4.6 mm×150 mm) purchased from Chiral Technology. Isopropanol (3%) and hexane (97%) containing 0.1% diethylamine was used as a mobile phase.

Example 1

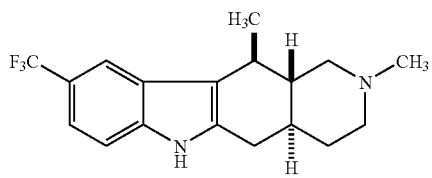

1

Compound 1 was synthesized in three steps according to Scheme 2 (*Acta. Chem. Scand. B,* 34, 1980, 136). To a mixture of NaH (2.44 g, 61 mmol, in 60% mineral oil) in ether (200 mL) at room temperature was added 1-methyl-4-piperidone (7.38 ml, 60 mmol) via syringe. After stirring for 1 h at room temperature, the reaction mixture was cooled to 0° C. 3-Penten-2-one (5.00 g, 60 mmol, contains 30% mesityl oxide) was added to the reaction mixture via syringe. The mixture was kept at 0° C. overnight. The reaction mixture was poured into aqueous NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 10–50% MeOH/EtOAc mixed with 0–20% conc. ammonia to yield enone i, wherein R is a methyl group, as a yellowish oil (2.66 g).

Scheme 2

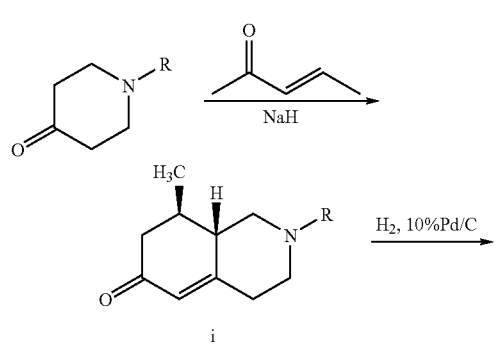

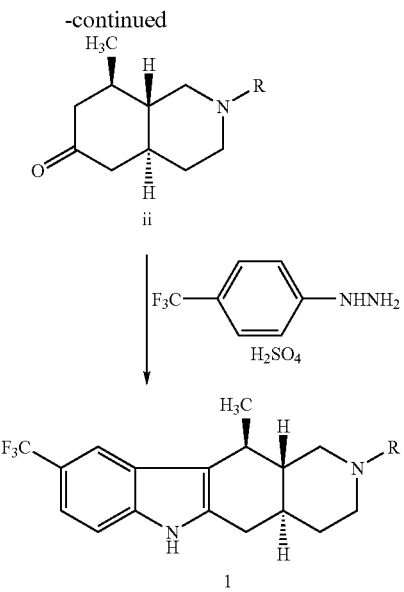

Enone i (2.60 g, 14.52 mmol) was stirred with 10% Pd/C (0.300 g) in EtOH (100 mL under balloon H$_2$ for 2.5 days. The reaction mixture was filtered. The filtrate was collected, concentrated by rotary evaporation and purified by flash chromatography on silica gel with a gradient elution of 20–40% MeOH/CH$_2$Cl$_2$ mixed with 0–20% conc. ammonia to yield the corresponding ketone ii as a yellowish solid (1.955 g).

A mixture of ketone ii (0.073 g, 0.4 mmol), 4-(trifluoromethyl)phenylhydrazine (0.070 g, 0.4 mmol), conc. H$_2$SO$_4$ (2 drops) and MeOH (2 mL) was stirred at room temperature overnight. Two more drops of H$_2$SO$_4$ were added and the mixture was heated to 80° C. in a sealed vial for 2 h. The mixture was cooled to room temperature, basified with aqueous NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 20–50% MeOH/CH$_2$Cl$_2$ mixed with 0–15% conc. ammonia to yield compound 1 as a pink solid (0.095 g). $^1$H NMR (DMSO-d$_6$): δ 11.20 (s, 1H), 7.78 (s, 1H), 7.43 (d, J=8.4 Hz, 1H), 7.28 (d, J=8.4 Hz, 1H), 3.20 (m, 1H), 2.83 (m, 1H), 2.74 (m, 1H), 2.60 (m, 1H), 2.19 (m, 1H), 2.26 (s, 3H), 1.92 (m, 1H), 1.81 (m, 1H), 1.70 (m, 1H), 1.38 (m, 3H), 1.36 (d, J=6.7 Hz, 1H). MS (ES): 323 [M+H]$^+$.

Alternatively, compound 1 can be prepared enantioselectively by performing a resolution of enone i. A general procedure for resolving enone i, wherein R is hydrogen, is described below.

To a stirred hot solution of the racemic isoquinolinone free base i (60.8 g, 0.239 mol) in 95% ethanol (150 mL) was added solution of di-O-p-toluoyl-L-tartaric acid (92.1 g, 0.124 mol) in hot ethanol (100 mL). Precipitation of the less soluble diastereomeric salt occurred soon after. The mixture was heated in a hot (80° C.) water bath with gentle stirring for 1 h, allowing some solvent to escape. The mixture was allowed to cool to room temperature slowly over several hours. The precipitate (52.9 g) was collected by filtration, triturated with hot 95% ethanol (150 mL) and collected by filtration after cooling. The solid salt collected was triturated with 100 mL 95% ethanol (hot), after cooling the solid was collected again by filtration. The free base (22.3 g, 0.087 mol) was obtained after neutralization with aqueous NaHCO₃ and extraction with AcOEt. The optical purity of the resolved product was determined to 96% ee by chiral HPLC analysis.

Example 2

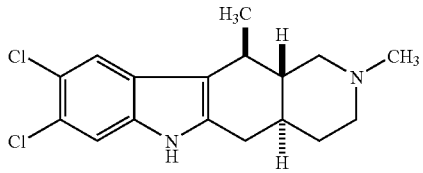

The title compound was synthesized according to Example 1, starting from ketone ii (Scheme 2), wherein R is a methyl group (0.063 g, 0.35 mmol), and 3,4-dichlorophenylhydrazine (0.960 g, 0.45 mmol). Cyclization was completed in 5 h at 80° C. Purification was performed by flash chromatography with a gradient elution of 20–50% MeOH/CH₂Cl₂ mixed with 0–15% conc. ammonia followed by reverse-phased HPLC to yield compound 2 as a yellowish solid (0.007 g). ¹H NMR (DMSO-d₆): δ 11.07 (s, 1H), 7.68 (s, 1H), 7.48 (s, 1H), 3.18 (m, 1H), 2.80 (m, 1H), 2.75 (m, 1H), 2.35 (m, 1H), 2.23 (s, 3H), 1.70 (m, 2H), 1.60 (m, 1H), 1.40 (m, 2H), 1.33 (d, J=6.6 Hz, 1H), 1.11 (m, 1H), 0.80 (m, 1H). MS (ES): 323 [M+H]⁺.

Example 3

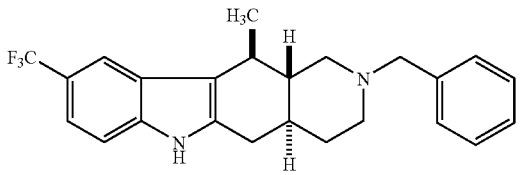

Compound 3 was synthesized according to Example 1, using 1-benzylpiperidin-4-one as the starting material. ¹H NMR (DMSO-d₆): δ 11.2 (s, 1H), 7.76 (s, 1H), 7.43 (s, 1H), 7.35 (bs, 5H), 3.59 (d, J=12 Hz, 1H), 3.46 (d, J=12 Hz, 1H), 3.26 (m, 2H), 2.83 (d, J=5.0 Hz, 1H), 2.75 (dd, J=15, 2 Hz, 1H), 2.60 (t, J=3 Hz, 1H), 2.42 (dd, J=15, 8 Hz, 1H), 1.95 (t, J=5 HZ, 1H), 1.80 (m, 2H), 1.46 (m, 2H), 1.46 (bs, 2H), 1.29 (d, J=6.6 Hz, 3H). MS (ES): 399 [M+H]⁺.

Example 4

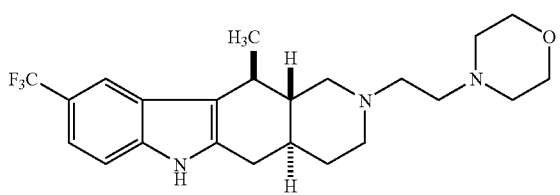

Compound 4 was prepared in two steps from compound 3, as follows.

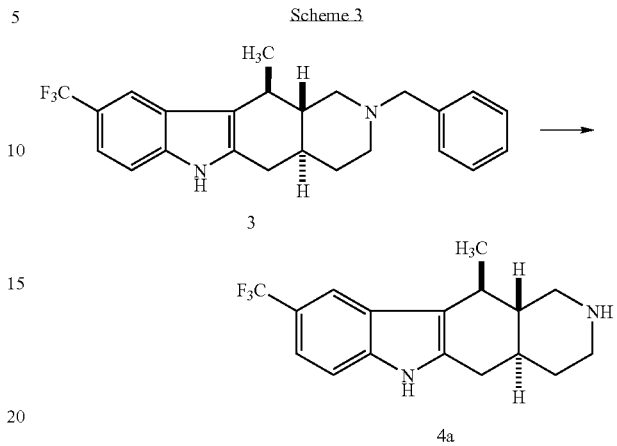

Step A. A mixture of compound 3 (3.80 g, 9.55 mmol), HCO₂NH₄ (3.03 g, 48 mmol), 10% Pd/C (0.380 g) and MeOH (150 mL) was refluxed for 7 h. The reaction mixture was cooled to room temperature, basified with saturated aqueous NaHCO₃ and extracted with EtOAc. The organic layer was separated, washed with brine, dried with anhydrous Na₂SO₄, concentrated by rotary evaporation and purified by flash chromatography on silica gel with a gradient elution of 20–50% MeOH—CH₂Cl₂ mixed with 0–15% conc. ammonia to yield the corresponding free amine (4a) as a yellowish solid (2.50 g). ¹H NMR (DMSO-d₆) δ 11.2 (s, 1H), 7.80 (s, 1H), 7.43 (d, J=5.4 Hz, 1H), 7.28 (d, J=5.4 Hz, 1H), 3.40 (d, J=6.0 Hz, 1H), 3.01 (d, J=8.0 Hz, 1H), 2.75 (d, J=10 Hz, 1H), 2.60 (m, 2H), 2.40 (m, 2H), 1.82 (d, J=8 Hz, 1H), 1.56 (m, 1H), 1.38 (d, J=5.4 Hz, 3H), 1.25 (m, 2H). MS (ES): 309 [M+H]⁺.

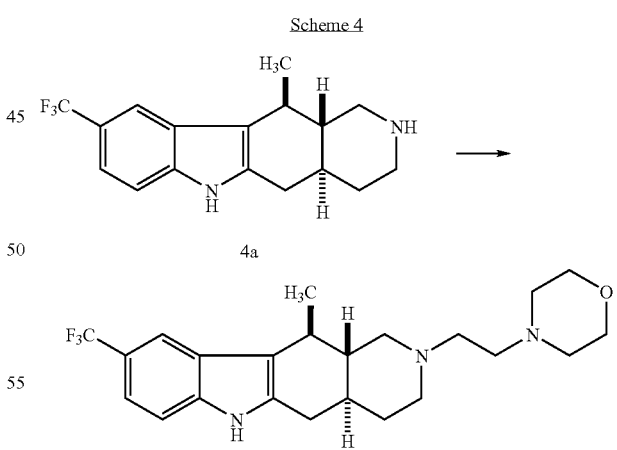

Step B. The product of step A (4a) (1.52 g, 4.94 mmol) was treated with N-2-chloroethylmorpholine hydrochloride (0.964 g, 5.19 mmol), NaI (0.22 g, 1.48 mmol), NaHCO₃ (1.03 g, 12.5 mmol), in acetone (50 mL) for 15 h at refluxing temperature. The reaction mixture was poured into aqueous NaHCO₃ and extracted with EtOAc. The organic layer was separated, washed with brine, dried with anhydrous Na$_2$SO$_4$, concentrated by rotary evaporation and purified by flash chromatography on silica gel with a gradient elution of 20–50% MeOH/EtOAc mixed with 0–15% conc. ammonia to yield compound 4 as a yellowish solid (0.68 g). $^1$H NMR (DMSO-d$_6$): δ 11.2 (s, 1H), 7.77 (s, 1H), 7.43 (d, J=6.4 Hz, 1H), 7.24 (d, J=6.4 Hz, 1H), 3.79 (bs, 4H), 2.90 (bs, 1H), 2.75 (d, J=5 Hz, 1H), 2.60 (d, J=2 Hz, 1H), 2.45 (m, 8H), 2.38 (bs, 4H0, 1.92 (m, 1H), 1.80 (m, 1H), 1.75 (m, 1H), 1.40 (m, 1H), 1.38 (d, J=5.0 Hz, 3H), 1.25 (m, 2H). MS (ES): 422 [M+H]$^+$.

Example 5

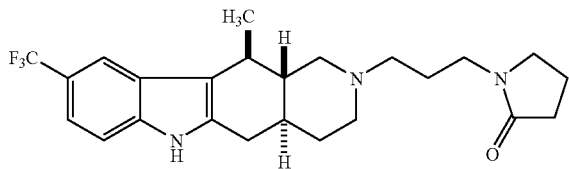

The secondary amine (4a) from step A of Example 4 (0.040 g, 0.13 mmol) was treated with 2-(3-chloropropyl) pyrrolidinone (0.100 g, 0.62 mmol), NaI (0.010 g, 0.07 mmol), NaHCO$_3$ (0.080 g, 0.095 mmol), DMF (1 mL) and MeOH (1 mL) in a sealed vial for 5 h at 90° C. The reaction mixture was poured into aqueous NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 20–50% MeOH/EtOAc mixed with 0–15% conc. ammonia to yield the target compound as a yellowish solid (0.017 g). $^1$H NMR (DMSO-d$_6$): δ 11.19 (s, 1H), 7.77 (s, 1H), 7.43 (d, J=8.4 Hz, 1H), 7.26 (d, J=8.4 Hz, 1H), 3.18–3.40 (m, 8H), 2.91 (m, 1H), 2.72 (m, 1H), 2.60 (m, 1H), 2.39 (m, 1H), 2.30 (m, 1H), 2.21 (m, 2H), 1.92 (m, 2H), 1.81 (m, 1H), 1.66 (m, 2H), 1.41 (m, 2H), 1.36 (d, J=6.7 Hz, 3H), 1.29 (m, 1H). MS (ES): 434 [M+H]$^+$.

Example 6

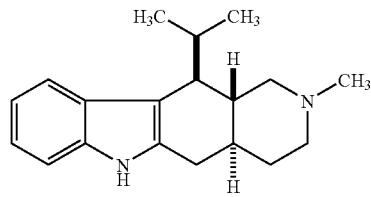

Compound 6 was synthesized according to Example 1, substituting 5-methyl-3-hexen-2-one for 3-penten-2-one. $^1$H NMR (DMSO-d$_6$): δ 10.68 (s, 1H), 7.36 (d, J=8.9 Hz, 1H), 7.23 (d, J=7.7 Hz, 1H), 6.95 (m, 1H), 6.88 (m, 1H), 3.15 (m, 1H), 2.87 (m, 1H), 2.61 (m, 2H), 2.27 (m, 5H), 1.97 (m, 1H), 1.79 (m, 2H), 1.52 (m, 2 H), 1.20 (m, 1H), 0.91 (d, J=7.0 Hz, 3H), 0.76 (d, J=6.9 Hz, 3H). MS (ES): 283 [M+H]$^+$.

Example 10

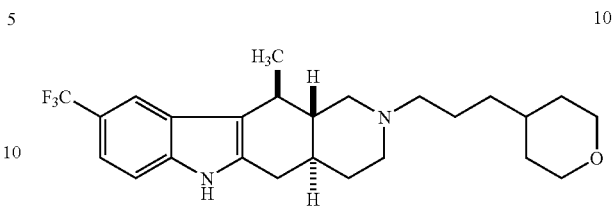

Compound 10 was synthesized following the procedure described in Example 5, substituting 3-(tetrahydropyran-4-yl)propyl tosylate for 1-(3-chloropropyl)pyrrolidin-2-one. $^1$H NMR of 10.HCl: (CD$_3$OD) δ 7.79 (s), 7.39 (d, J=8.6 Hz, 1H), 7.30 (d, J=8.6 Hz, 1H), 3.95 (dd, J=11, 3.7 Hz, 2H), 3.88 (d, J=11.2 Hz, 1H), 3.66 (d, J=10.3 Hz, 1H), 3.42 (td, J=12.0, 1.7 Hz, 2H), 3.20 (m, 2H), 3.03 (m, 1H), 2.89 (dd, J=16.0, 4.5 Hz, 2H), 2.82 (t, J=6.8 Hz, 1H), 2.53 (dd, J=16.2, 11.4 Hz, 1H), 2.20 (d, J=13.4 Hz, 1H), 1.86 (m, 3H), 1.74 (q, J=12.0 Hz, 1H), 1.70 (m, 3H), 1.61 (m, 1H), 1.50 (d, J=6.7 Hz, 3H), 1.37 (q, J=7.8 Hz, 2H), 1.30 (qd, J=12.1, 4.3 Hz, 2H). MS (ES) 435 [M+H]$^+$.

3-(Tetrahydropyan-4-yl)propyl tosylate can be conveniently prepared using the following procedure or a variation thereof.

Tetrahydropyan-4-ylmethanol was obtained from the reduction of tetrahydropyran-4-carboxylic acid with borane or from the reduction of methyl tetrahydropyran-4-ylcarboxylate with LiAlH$_4$.

To a solution of tetrahydropyran-4-ylmethanol (10 g, 86.2 mmol) in CH$_2$Cl$_2$ (170 mL) was added p-toluenesulfonyl chloride (17.26 g, 90.5 mmol), triethylamine (9.58 g, 94.8 mmol) and DMAP (0.527 g, 4.31 mmol). The mixture was stirred at room temperature for 16 h. Dilute aqueous NaHCO$_3$ was added and layers were separated. The organic layer was washed with brine, dried over MgSO$_4$ and concentrated to give the tetrahydropyan-4-ylmethyl tosylate as a solid.

To a suspension of CuBr (22.8 g, 158.9 mmol) in anhydrous ether cooled in an ice-water bath was added a solution of allylmagnesium bromide (1M in ether, 328 mL, 318 mmol), followed by a solution of tetrahydropyan-4-ylmethyl tosylate in ether (200 mL) and THF (100 mL). The mixture was stirred vigorously at 0° C. for 4 h (additional Grignard reagent can be added to drive the reaction to completion). The reaction was quenched by slow addition of saturated aqueous NH$_4$Cl. The mixture was filtered through a Celite pad, rinsing with ether. The two layers of the filtrate were separated and the aqueous layer was extracted with ether. The combined organic layers were washed with saturated NaHCO$_3$ and brine, and dried over Na$_2$SO$_4$. After filtration and careful removal of volatile solvent, the residual material was distilled under slightly reduced pressure to give the corresponding olefin as colorless oil (15 g).

A solution of the olefin (15 g, 107 mmol) in CH$_2$Cl$_2$ (210 mL) was cooled in a dry ice-acetone bath. Ozone was bubbled through the solution until the complete disappearance of starting material judged by TLC. A nitrogen stream was passed through the reaction mixture for a few minutes to drive away the excess ozone. The reaction mixture was diluted with ethanol (100 mL). NaBH$_4$ (14.2 g, 375 mmol) was added to the reaction mixture and stirring was continued while the temperature was allowed to rise to 0° C. At the completion of the reaction, water was added. After standard aqueous work-up, the corresponding alcohol was obtained as a colorless oil (15 g). The alcohol was converted to 3-(tetrahydropyran-4-yl)propyl tosylate by treatment with tosyl chloride in the presence of a base, e.g., triethylamine in CH$_2$Cl$_2$.

Example 11

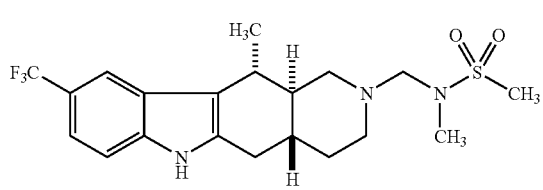

11

Compound 11 was synthesized following the procedure described in Example 5, substituting N-(3-methanesulfonyloxy-propyl)-N-methyl-methanesulfonamide for 1-(3-chloropropyl)pyrrolidin-2-one. The corresponding HCl salt was prepared by the addition of 1N HCl in ether to a solution of the product in ethyl acetate. The HCl salt precipitated out on concentration. 1H NMR of 11.HCl: (CDCl$_3$) δ 11.8 (s, 1H), 7.66 (s, 1H), 7.56 (s, 1H), 7.30 (d, J=8.6 Hz, 1H), 7.18 (d, J=8.6 Hz, 1H), 3.56 (d, J=11 Hz, 1H), 3.42 (d, J=12 Hz, 1H), 3.16 (bs, 2H), 2.92 (m, 2H), 2.36 (m, 2H), 2.12–2.23 (m, 4H), 1.99 (q, J=11.7 Hz, 1H), 1.72 (d, J=12 Hz, 1H), 1.56 (bs, 2H), 1.30 (m, 1H), 0.98 (d, J=6.3 Hz, 3H). MS (ES) 458 [M+H]$^+$.

Example 12

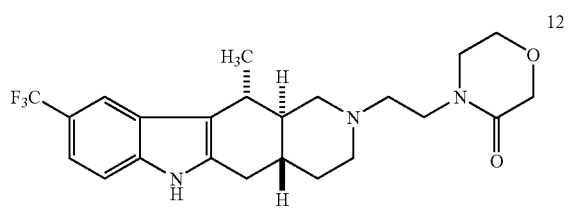

12

Compound 12 was synthesized following the procedure described in Example 5, substituting 4-(2-chloro-ethyl)-morpholin-3-one for 1-(3-chloropropyl)pyrrolidin-2-one. $^1$H NMR (DMSO-d$_4$) δ 11.2 (s, 1H), 7.77 (s, 1H), 7.44 (d, J=8.4 Hz, 1H), 7.28 (d, J=8.6 Hz, 1H), 4.02 (s, 2H), 3.81 (t, J=4.7 Hz, 2H), 3.50 (m, 1H), 3.42 (t, J=4.7 Hz, 2H), 3.30 (m, 2H), 2.92 (m, 1H), 2.75 (d, J=12 Hz, 1H), 2.60 (m, 1H), 2.40 (m, 2H), 1.91 (d, J=8.4 Hz, 1H), 1.85 (m, 1H), 1.40 (m, 2H), 1.38 (d, J=6.6 Hz, 3H), 1.25 (m, 1H). MS (ES) 436 [M+H]$^+$.

Example 13

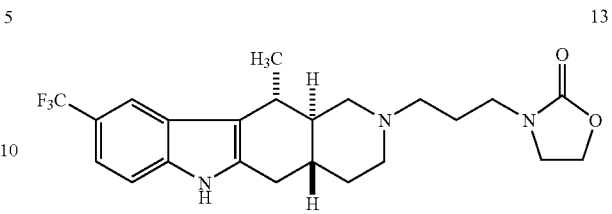

13

Compound 13 was synthesized following the procedure described in Example 5, substituting 3-(3-chloro-propyl)-oxazolidin-2-one for 1-(3-chloropropyl)pyrrolidin-2-one. $^1$H NMR (d$_6$-DMSO) δ 11.2 (s, 1H), 7.77 (s, 1H), 7.43 (d, J=8.4 Hz, 1H), 7.27 (d, J=8.6 Hz, 1H), 4.25 (t, J=8.0 Hz, 2H), 3.54 (t, J=8.0 Hz, 2H), 3.34 (m, 2H), 3.24 (t, J=12 Hz, 1H), 3.19 (t, J=7.0 Hz, 2H), 2.96 (d, J=12 Hz, 1H), 2.60 (t, J=7.0 Hz, 1H), 2.39 (m, 3H), 1.95 (m, 1H), 1.89 (d, J=7.0 Hz, 1H), 1.70 (t, J=7.0 Hz, 2H), 1.40 (m, 1H), 1.36 (d, J=6.6 Hz, 2H), 1.25 (m, 1H). MS (ES) 436 [M+H]$^+$.

Example 14

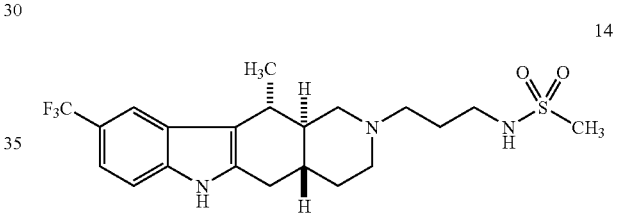

14

Compound 14 was prepared in three steps from compound 4a, as follows.

Step A. A mixture of compound 4a, (5.5 g, 17.6 mmol), N-(3-bromopropyl)phthalimide (5.5 g, 20.5 mmol), sodium bicarbonate (5.0 g, 63.1 mmol) and sodium iodide (0.50 g, 3.33 mmol) in DMF (50 mL) was heated at 90° C. overnight. The reaction mixture was diluted with ethyl acetate, washed with brine. The organic layer was dried over MgSO$_4$, filtered and concentrated. The crude product was purified by flash chromatography on silica gel, eluting with a solvent system consisting of CH$_2$Cl$_2$—MeOH—NH$_4$OH in 40:1:0.1 ratio by volume to give the desired phthalimide intermediate.

Step B. The product from step A was dissolved in ethanol (75 mL) and treated with hydrazine monohydrate (15 mL) at reflux overnight. Upon cooling to room temperature, the precipitate was removed by filtration and the filtrate was concentrated, and purified by flash chromatography on silica gel, eluting with CH$_2$Cl$_2$—MeOH—NH$_4$OH in 10:1:0.1 ratio by volume to give the corresponding amine.

Step C. Compound 14 was prepared by treating a sample of the amine compound from step B with methanesulfonyl chloride in the presence of a tertiary amine base such as triethylamine. $^1$H NMR (DMSO-d$^6$) δ 11.2 (s, 1H), 7.77 (s, 1H), 7.43 (d, J=8.4 Hz, 1H), 7.27 (d, J=8.6 Hz, 1H), 7.00 (bs, 1H), 3.31 (m, 1H), 3.30 (m, 2H), 2.90 (s, 3H), 2.78 (d, J=12

Hz, 1H), 2.60 (m, 1H), 2.40 (m, 3H), 1.95 (m, 2H), 1.68 (m, 3H), 1.45 (m, 2H), 1.37 (d, J=6.6 Hz, 3H), 1.25 (, 1H). MS (ES) 444 [M+H]+.

Example 15

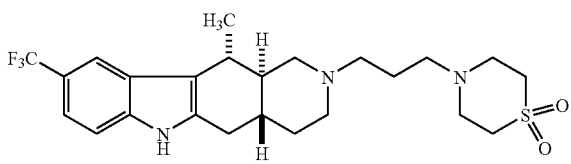

Compound 15 was prepared by treating a sample of the amine from step B of Example 14 with vinylsulfone in ethanol at refluxing temperature for 30 min. $^1$H NMR (d$_6$-DMSO) δ 11.2 (s, 1H), 7.77 (s, 1H), 7.43 (d, J=8.4 Hz, 1H), 7.27 (d, J=8.6 Hz, 1H), 3.33 (m, 1H), 3.08 (t, J=5.2 Hz, 4H), 2.92 (m, 1H), 2.88 (t, J=5.2 Hz, 4H), 2.78 (d, J=12 Hz, 1H), 2.60 (m, 1H), 2.40 (m, 2H), 1.89–1.96 (m, 2H), 1.62 (m, 3H), 1.42 (m, 2H), 1.38 (d, J=6.6 Hz, 3H), 1.30 (m, 1H). MS (ES) 484 [M+H]+.

Example 16

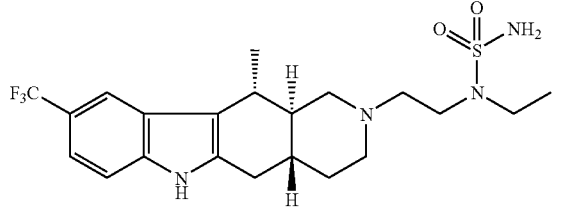

Compound 16 was prepared in a few steps following conditions similar to those described in Example 14. The final sulfonyl urea was formed using the conditions described below.

At room temperature, the N-(2-ethylaminoethyl) derivative of Compound 4a (55 mg, 0.146 mmol) was dissolved with 10 mL p-dioxane. To the stirred solution, 140 mg (1.46 mmol) of sulfonamide was added. After being heated for 2 h at 110° C. in an oil bath, the reaction mixture was diluted with 20 mL ethyl acetate and washed with sat. 20 mL NaHCO$_3$. The organic layer was separated, dried over Na$_2$SO$_4$, and concentrated. The residue was purified by HPLC to afford compound 16 (30 mg). $^1$H NMR (400 MHz, CD$_3$OD) δ 7.79 (s, 1H), 7.40 (d, 1H, J=8.8 Hz), 7.29 (d, 1H, J=8.8 Hz), 2.5–4.1 (m, 10H), 1.5 (d, 3H, J=6.8 Hz), 1.1–2.2 (m, 10H).

Examples 17–25

Compounds 17–25 (see Table 1 below) were prepared using the following procedure.

Starting from a sample of the amine from Example 14, Step B (778 mg, 2.13 mmol) in dioxane (20 mL) at 0° C. was added Et$_3$N (326 μL, 2.34 mmol) and p-nitrophenylchloroformate (429 mg, 2.13 mmol). The reaction mixture was warmed to r.t. and stirred for an additional 4 h or until the starting material was completely converted to the activated carbamate as evident by LCMS (M+1=531). The solution was filtered to remove any precipitation that had formed, an additional 3 equiv. of Et$_3$N (890 μL, 6.4 mmol) were added and the solution was diluted with dioxane to a total volume of 50 mL. Aliquots of the stock solution were dispensed into a 48 deep well Robbin's block (1 mL, 0.043 mmol of activated carbamate per well). Solutions of 48 primary and secondary amines were made in DMF (1 mL, 0.047 mmoles) and dispensed into the Robbin's block containing the activated carbamate. The Robbin's block was sealed, placed in a Robbin's oven and slowly rotated at 50° C. for 16 h. Upon completion of the reaction the solvent was evaporated, the residue dissolved in 1 mL of DMSO, and purified by automated reverse phase preparatory HPLC to provide, on average, 10 mg of product of >90% purity.

TABLE 1

| Compound | R | ES-MS [M+H]+ |
|---|---|---|
| 17 | 2,4-dimethoxyphenyl-N(Me)- | 545.6 |
| 18 | cyclohexyl-N(Me)- | 491.6 |
| 19 | isopropyl-N(Me)- | 451.5 |
| 20 | 2,3-dihydroxypropyl-N(Me)- | 483.5 |
| 21 | 1-methylpyrrol-2-ylmethyl-piperidin-4-yl-N(Me)- | 585.7 |
| 22 | 2-ethoxybenzyl-piperidin-4-yl-N(Me)- | 626.8 |

TABLE 1-continued

| Compound | R | ES-MS [M+H]+ |
|---|---|---|
| 23 | | 586.7 |
| 24 | | 520.7 |
| 25 | | 522.6 |

Example 26

The MCHR modulatory activity of the compounds of the invention can be assessed using the in vitro and in vivo assay methods described above.

Exemplary in vitro methods include fluorometric imaging plate reader (FLIPR) functional assays (see, e.g., *G Protein-Coupled Receptors* (1999) pp. 105–108 (T. Haga, G. Bernstein, eds.) CRC Press; Lembo et al. (1999) *Nature Cell Biol.* 1:267–271; Saito et al. (1999) *Nature* 400:265–269; Wood et al. (2000) *Eur. J. Pharmacol.* 396:1–8 and Miller et al. (1999) *J. Biomol. Screen.* 4:249–258) and radioligand binding assays (see, e.g., *Receptor Binding Techniques* (1999) pp. 37–47 (M. Keen, ed.) Humana Press; Buckley et al. (1989) *Mol. Pharmacol.* 35:469–476; Mihara et al. (1994) *J. Pharmacol. Exp. Ther.* 268:1122–1128; Newman et al. (2000) *Eur. J. Pharmacol.* 397:255–262 and Audinot et al. (2001) *Br. J. Pharmacol.* 133:371–378).

Exemplary compounds demonstrated MCHR1 modulatory activity.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound or a pharmaceutically acceptable salt, hydrate, solvate or prodrug thereof, wherein said compound is selected from the group consisting of:

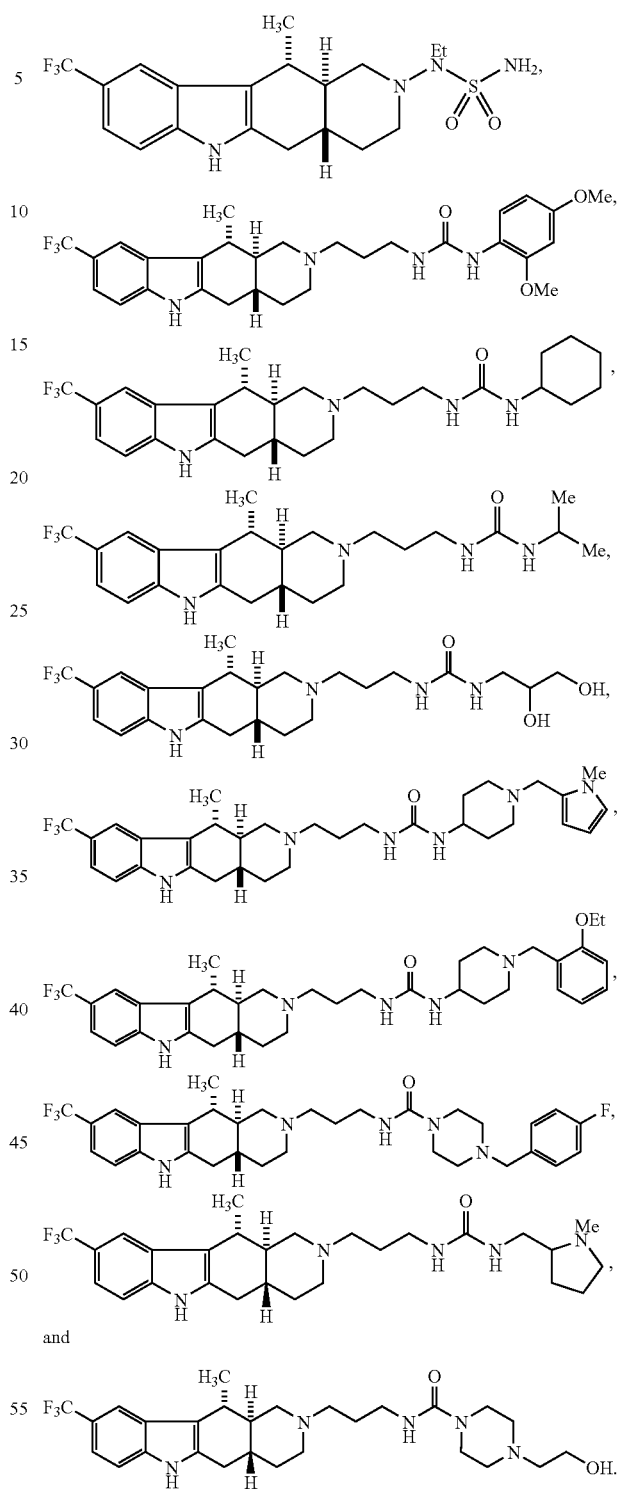

and

2. A pharmaceutical composition comprising a pharmaceutically acceptable carrier or excipient and a compound of claim 1.

* * * * *